US007746474B2

(12) United States Patent
Oda

(10) Patent No.: US 7,746,474 B2
(45) Date of Patent: Jun. 29, 2010

(54) COLOR IDENTIFYING DEVICE FOR IDENTIFYING COLORS OF REACTION SURFACES PRODUCED BY CHEMICAL REACTION AND GAS IDENTIFYING DEVICE

(75) Inventor: Naoki Oda, Tokyo (JP)

(73) Assignee: NEC Corporation, Tokyo (JP)

( * ) Notice: Subject to any disclaimer, the term of this patent is extended or adjusted under 35 U.S.C. 154(b) by 541 days.

(21) Appl. No.: 11/723,656

(22) Filed: Mar. 21, 2007

(65) Prior Publication Data

US 2007/0222992 A1    Sep. 27, 2007

(30) Foreign Application Priority Data

Mar. 22, 2006    (JP)    ............... 2006-078809

(51) Int. Cl.
*G01J 3/46*    (2006.01)
(52) U.S. Cl. .................. 356/402; 356/407; 356/437
(58) Field of Classification Search ............... 356/402, 356/406, 425, 416, 419, 437; 422/86; 436/164
See application file for complete search history.

(56) References Cited

U.S. PATENT DOCUMENTS 3,756,725 A  *  9/1973  Manring ............... 356/425

| | | | | |
|---|---|---|---|---|
| 4,681,454 A | * | 7/1987 | Breemer | ............... 356/402 |
| 5,091,642 A | * | 2/1992 | Chow et al. | ............... 250/226 |
| 5,706,083 A | * | 1/1998 | Iida et al. | ............... 356/328 |
| 6,228,657 B1 | | 5/2001 | Genovese et al. | |
| 7,277,019 B2 | * | 10/2007 | Povenmire | ............... 340/601 |
| 7,499,154 B2 | * | 3/2009 | Stock et al. | ............... 356/73 |
| 2006/0008919 A1 | * | 1/2006 | Boay et al. | ............... 436/164 |

* cited by examiner

*Primary Examiner*—L. G Lauchman
(74) *Attorney, Agent, or Firm*—McGinn IP Law Group, PLLC

(57) ABSTRACT

A color identifying device includes a mount block, a color detector, a lens and a color identifier. A reactive board having a plurality of surfaces to be measured in respective predetermined positions is mounted in the mount block. The color detector has a plurality of color measuring areas corresponding respectively to the reaction surfaces of the reactive board mounted in the mount block. The lens forms images of the surfaces of the reactive board mounted in the mount block on the respective color measuring areas. The color identifier identifies the colors of the surfaces based on output signals from the corresponding color measuring areas.

21 Claims, 16 Drawing Sheets

Fig. 13

7b SPECTRUM DATABASE

7b3 COLOR INFORMATION

| CHEMICAL REAGENT NAMES (7b1) | GAS IDENTIFYING INFORMATION (7b2) | COLOR CHANGE INFORMATION (SPECTRUM INFORMATION) | |
|---|---|---|---|
| | | λ | INTENSITY |
| A | a | 1 | aaa |
| | | 2 | bbb |
| | | 3 | ccc |
| | | ⋮ | ⋮ |
| | | 256 | nnn |
| B | b | 1 | aba |
| | | 2 | cdc |
| | | ⋮ | ⋮ |
| | | 256 | aaa |
| C | c | 1 | bbb |
| | | 2 | ddd |
| | | ⋮ | |
| | | 256 | eee |

Fig. 15

7cd STORAGE AREA

| λ | DETECTED VALUE | | | | Sb(∧) | ∧ (BAND) |
|---|---|---|---|---|---|---|
| | S0 | S1 | SX | S | | |
| 1 | · | · | · | · | | |
| 2 | · | · | · | · | · | \| |
| 3 | · | · | · | · | | |
| 4 | · | · | · | · | | |
| ⋮ | ⋮ | ⋮ | ⋮ | ⋮ | ⋮ | |
| | | | | | · | 64 |
| 256 | · | · | · | · | | |

Binning = 4

COLOR IDENTIFYING DEVICE FOR IDENTIFYING COLORS OF REACTION SURFACES PRODUCED BY CHEMICAL REACTION AND GAS IDENTIFYING DEVICE

This application is based upon and claims the benefit of priority from Japanese Patent Application No. 2006-078809 filed on Mar. 22, 2006, the content of which is incorporated by reference.

BACKGROUND OF THE INVENTION

1. Field of the Invention

The present invention relates to a color identifying device and a gas identifying device, and more particularly to a color identifying device for identifying colors of reaction surfaces which are produced by a chemical reaction and a gas identifying device.

2. Description of the Related Art

There have heretofore been known gas detecting devices for causing a chemical reaction between a gas such as a toxic gas and chemical reagents to change the colors of the chemical reagents. For example, U.S. Pat. No. 6,228,657B1 discloses an M256 chemical agent detection kit.

The gas detecting device includes a plurality of ampules containing respective chemical reagents of different types and a plurality of mediums (reaction surfaces). When the ampules are crushed, the chemical reagents contained therein flow into the mediums.

The chemical reagents, as they flow into the mediums, chemically react with a gas that is held in contact with the mediums. The chemical reaction causes the chemical reagents to change their colors, and the mediums also change their colors depending on the color changes of the chemical reagents.

The user of the gas detecting device introduces different chemical reagents into the respective mediums, and recognizes the concentration of the gas based on the color changes of the mediums.

There are also known color identifying devices in the art. The user can objectively determine the colors of the mediums (chemical reagents) of the gas detecting device by using a color identifying device to identify the colors of the mediums.

One known color identifying device has three photodetectors and three optical filters associated respectively with the photodetectors.

If it is assumed that the photodetectors produce respective outputs X, Y, Z, then the color identifying device calculates values $x=X/(X+Y+Z)$, $y=Y/(X+Y+Z)$, and $z=Z/(X+Y+Z)$. Of these values x, y, z, two, e.g., the values x and y, are plotted on a chromaticity diagram, and a color is determined from the position of the values on the chromaticity diagram.

U.S. Pat. No. 6,228,657B1 also reveals a reader device for outputting a signal depending on the color of a measuring surface (medium) using three photodiodes or a single color CCD sensitive to the colors of R, G, B (red, green, and blue).

The conventional color identifying device can measure the color of one medium only in one measuring cycle. If the user uses the conventional color identifying device to measure the colors of a plurality of mediums, then the user have to measure the colors of the mediums separately.

If the reader device revealed in U.S. Pat. No. 6,228,657B1 is used to measure the colors of a plurality of measuring surfaces at a time, the reader device needs to have three photodiodes or a single color CCD for each of the measuring surfaces. Consequently, as the number of measuring surfaces to be measured at a time increases, the number of photodiodes or color CCDs used also increases, resulting in an increased number of parts of the reader device.

SUMMARY OF THE INVENTION

It is an object of the present invention to provide a color identifying device and a gas identifying device which are capable of measuring the colors of a plurality of measuring surfaces at a time without the need for a number of parts commensurate with the number of measuring surfaces.

To achieve the above object, a color identifying device according to the present invention has a mount block, a color detector, a lens, and a color identifier.

A board to be measured which has a plurality of surfaces to be measured in predetermined positions, respectively, is mounted in the mount block.

The color detector has a plurality of color measuring areas corresponding respectively to said surfaces while said board is mounted in said mount block.

The lens forms respective images of said surfaces of said board mounted on said mount block, respectively on said color measuring areas corresponding respectively to said surfaces.

The color identifier identifies colors of said surfaces which correspond respectively to said color measuring areas, based on output signals from said color measuring areas corresponding respectively to said surfaces.

With the above arrangement, when the user places the board to be measured in the mount block, the colors of the surfaces to be measured are measured. The number of parts of the color identifying device is prevented from increasing in a manner to be commensurate with the number of reaction surfaces.

The output signals from said color measuring areas should preferably represent spectrums of the colors of said surfaces which correspond respectively to said color measuring areas.

The colors of the surfaces can thus be identified based on the spectrums of the colors. Therefore, the colors of the surfaces can be identified with high accuracy.

The output signals from said color measuring areas should preferably represent three components of the colors of said surfaces which correspond respectively to said color measuring areas.

Specifically, said output signals from said color measuring areas should preferably represent red, green, and blue components of the colors of said surfaces which correspond respectively to said color measuring areas.

The colors of the surfaces can thus be identified based on the three components, e.g., the red, green, and blue components, of the colors of said surfaces. Therefore, the colors of the surfaces can be identified with high accuracy.

According to the present invention, a gas identifying device has a mount block, a color detector, a lens, and a gas identifier.

A reactive board having a plurality of reaction surfaces disposed in predetermined positions, respectively, is mounted in a mount block. The reaction surfaces have colors variable by chemical reactions between a gas to be identified and chemical reagents.

The color detector has a plurality of color measuring areas corresponding respectively to said reaction surfaces while said board is mounted on said mount block.

The lens forms respective images of said reaction surfaces of said board mounted on said mount block, respectively on said color measuring areas corresponding respectively to said surfaces.

The gas identifier identifies said gas based on output signals from said color measuring areas corresponding respectively to said surfaces.

With the above arrangement, when the user places the reactive board in the mount block, the gas to be identified is identified based on the colors of the reaction surfaces. The number of parts of the gas identifying device is prevented from increasing in a manner to be commensurate with the number of reaction surfaces.

The output signals from said color measuring areas should preferably represent spectrums of the colors of said reaction surfaces which correspond respectively to said color measuring areas.

The colors of the reaction surfaces can thus be identified based on the spectrums of the colors. Therefore, the colors of the reaction surfaces can be identified with high accuracy.

The output signals from said color measuring areas should preferably represent three components of the colors of said reaction surfaces which correspond respectively to said color measuring areas.

Specifically, said output signals from said color measuring areas should preferably represent red, green, and blue components of the colors of said reaction surfaces which correspond respectively to said color measuring areas.

The colors of the reaction surfaces can thus be identified based on the three components, e.g., the red, green, and blue components, of the colors of said reaction surfaces. Therefore, the colors of the reaction surfaces can be identified with high accuracy.

The above and other objects, features, and advantages of the present invention will become apparent from the following description with reference to the accompanying drawings which illustrate an example of the present invention.

BRIEF DESCRIPTION OF THE DRAWINGS

FIG. 13 is a diagram showing an example of data stored in a spectrum database of the gas identifying device shown in FIG. 8;

FIG. 15 is a diagram showing an example of spectral data representative of color changes of a reaction surface which are stored in the memory;

DETAILED DESCRIPTION OF THE PREFERRED EMBODIMENTS

Figure 1:
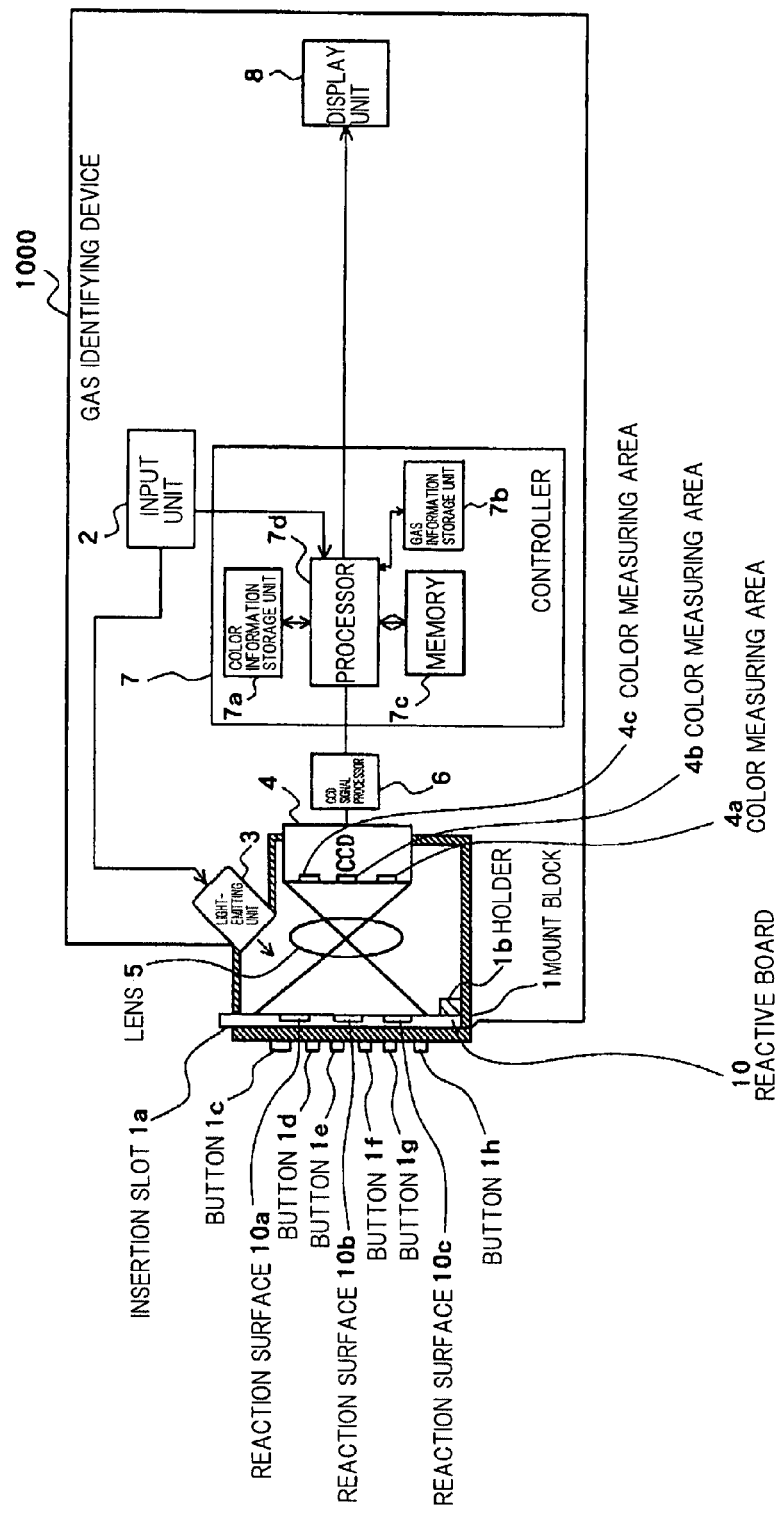
FIG. 1 is a block diagram of a gas identifying device according to the present invention.

FIG. 1 shows in block form gas identifying device 1000 according to the present invention.

As shown in FIG. 1, gas identifying device 1000 comprises mount block 1, input unit 2, light-emitting unit 3, CCD 4, lens 5, CCD signal processor 6 including an ADC (analog-to-digital converter), controller 7, and display unit 8.

Controller 7 comprises color information storage unit 7a, gas information storage unit 7b, memory 7c, and processor 7d.

Reactive board 10, which is an example of a board to be measured, is mounted in mount block 1.

Reactive board 10 has a plurality of reaction surfaces (surfaces to be measured) 10a, 10b and 10c. Each of reaction surfaces 10a, 10b and 10c is disposed in a predetermined position on reactive board 10.

Figure 2:
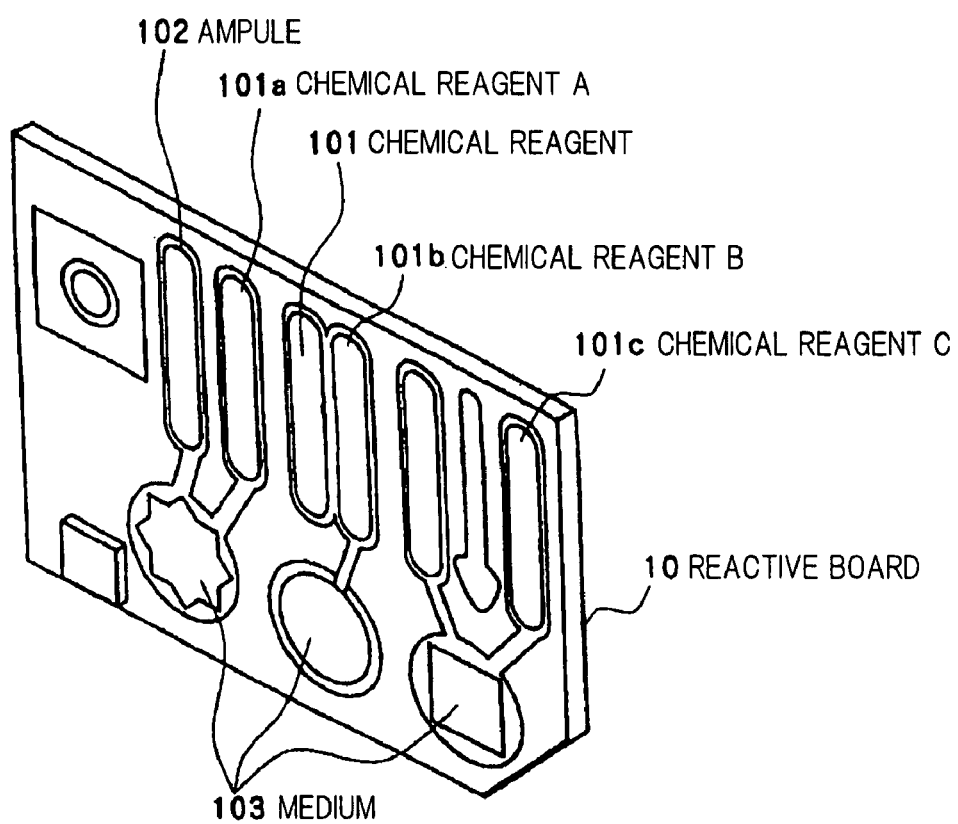
FIG. 2 is a perspective view of a reactive board of the gas identifying device shown in FIG. 1.

FIG. 2 shows reactive board 10 in perspective.

As shown in FIG. 2, reactive board 10 has a plurality of chemical reagents 101 which are different from each other, a plurality of ampules 102, and a plurality of mediums 103. Ampules 102 contain chemical reagents 101, respectively, which are of different types. Mediums 103 are respective sheets of paper. When ampules 102 are crushed, chemical reagents contained therein flow into mediums 103. Mediums 103 provide reaction surfaces (surfaces to be measured) 10a, 10b and 10c.

Reactive board 10 includes chemical reagent 101a titled "A", chemical reagent 101b titled "B", and chemical reagent 101c titled "C".

When each chemical reagent 101 flows into medium 103, it chemically reacts with a gas, e.g., a gas to be identified, that is held in contact with medium 103. Chemical reagent 101 and medium 103 change their colors due to the chemical reaction with the gas. The M256 chemical agent detection kit disclosed in U.S. Pat. No. 6,228,657B1, for example, may be used as reactive board 10.

In FIG. 1, gas identifying device 1000 identifies the gas to be identified based on the colors of chemical reagents 101 which have chemically reacted with the gas on reactive board 10. Stated otherwise, gas identifying device 1000 identifies the gas to be identified based on the colors of the reaction surfaces where the chemical reaction has occurred.

Mount block 1 has insertion slot 1a, holder 1b, and a plurality of buttons 1c through 1h.

Reactive board 10 is inserted through insertion slot 1a into mount block 1 and is held in mount block 1 by holder 1b.

When reactive board 10 is held in mount block 1 by holder 1b, buttons 1c through 1c on mount block 1 are aligned respectively with ampules 102 on reactive board 10. When the user presses one of buttons 1c through 1h, the pressed button pushes and crushes the ampule that is aligned therewith.

Input unit 2 is an operation switch for receiving an input action of the user, which may represent an instruction to emit light from light-emitting unit 3, for example.

When input unit 2 receives a light-emitting instruction, input unit 2 transmits the light-emitting instruction to light-emitting unit 3 and processor 7d.

In response to the light-emitting instruction, light-emitting unit 3 emits and applies light to reaction surfaces 10a through 10c. Light-emitting unit 3 preferably, but not necessarily, comprises a halogen lamp or an incandescent lamp.

Reaction surfaces 10a through 10c reflect the light applied from light-emitting unit 3. If a reaction surface contains chemical reagent 101 that has chemically reacted with the gas to be identified, then the light reflected by the reaction surface exhibits the color of chemical reagent 101 that has chemically reacted with the gas to be identified.

Mount block 1 prevents other lights that are different from the light emitted from light-emitting unit 3 from irradiating reactive board 10.

CCD 4 is an example of color detector used in gas identifying device 1000. The color detector may comprise another device such as a CMOS sensor, for example, rather than a CCD.

Figure 3:
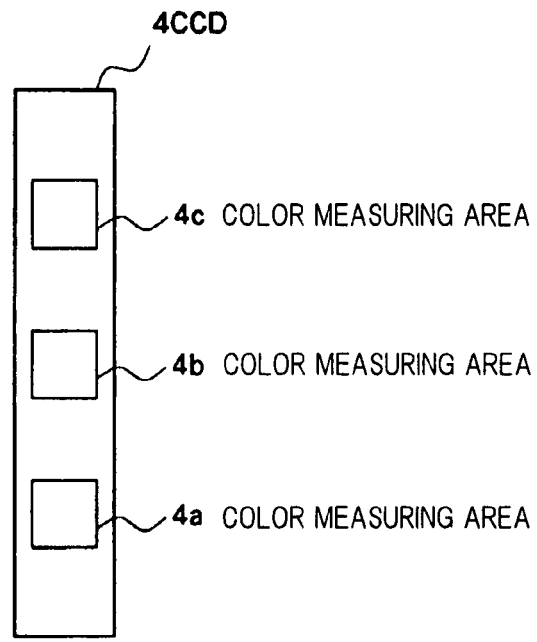
FIG. 3 is a view showing a CCD of the gas identifying device shown in FIG. 1.

FIG. 3 shows CCD 4 by way of example. Those parts of CCD 4 shown in FIG. 3 which are identical to those shown in FIG. 1 are denoted by identical reference characters.

As shown in FIG. 3, CCD 4 has a plurality of color measuring areas 4a, 4b and 4c corresponding respectively to reaction surfaces 10a, 10b and 10c of reactive board 10 mounted in mount block 1. Specifically, color measuring area 4a corresponds to reaction surface 10a, color measuring area 4b to reaction surface 10b, and color measuring area 4c to reaction surface 10c. Each of color measuring areas 4a, 4b and 4c comprises an array of photodetectors.

As shown in FIG. 1, lens 5 forms images of reaction surfaces 10a through 10c of reactive board 10 mounted in mount block 1 on respective color measuring areas 4a through 4c.

Figure 4:
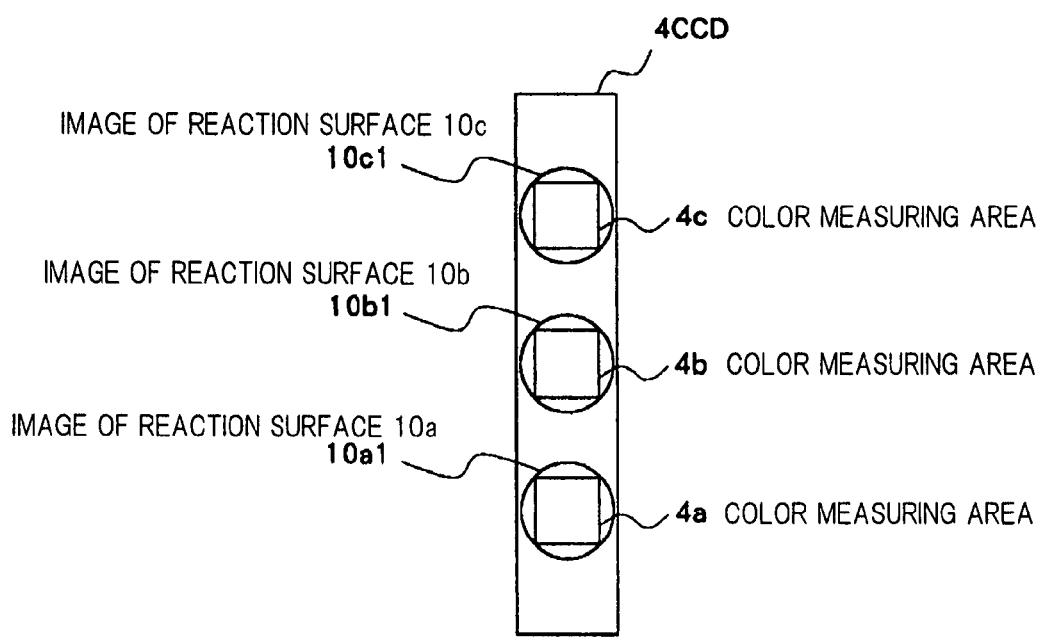
FIG. 4 is a view showing the CCD with images formed thereon.

FIG. 4 shows CCD 4 on which the images of reaction surfaces 10a through 10c are formed by lens 5. Those parts of CCD 4 shown in FIG. 4 which are identical to those shown in FIG. 1 are denoted by identical reference characters.

In FIG. 4, image 10a1 of reaction surface 10a is formed on color measuring area 4a, image 10b1 of reaction surface 10b on color measuring area 4b, and image 10c1 of reaction surface 10c on color measuring area 4c.

If CCD 4 comprises a color CCD, then an output signal from color measuring area 4a varies depending on the color of reaction surface 10a, an output signal from color measuring area 4b varies depending on the color of reaction surface 10b, and an output signal from color measuring area 4c varies depending on the color of reaction surface 10c.

If CCD 4 comprises a CCD having a linear variable filter (LVF) on its detecting surface, then an output signal from color measuring area 4a varies depending on the color of reaction surface 10a (the spectrum of the color), an output signal from color measuring area 4b varies depending on the color of reaction surface 10b (the spectrum of the color), and an output signal from color measuring area 4c varies depending on the color of reaction surface 10c (the spectrum of the color).

Figure 5:
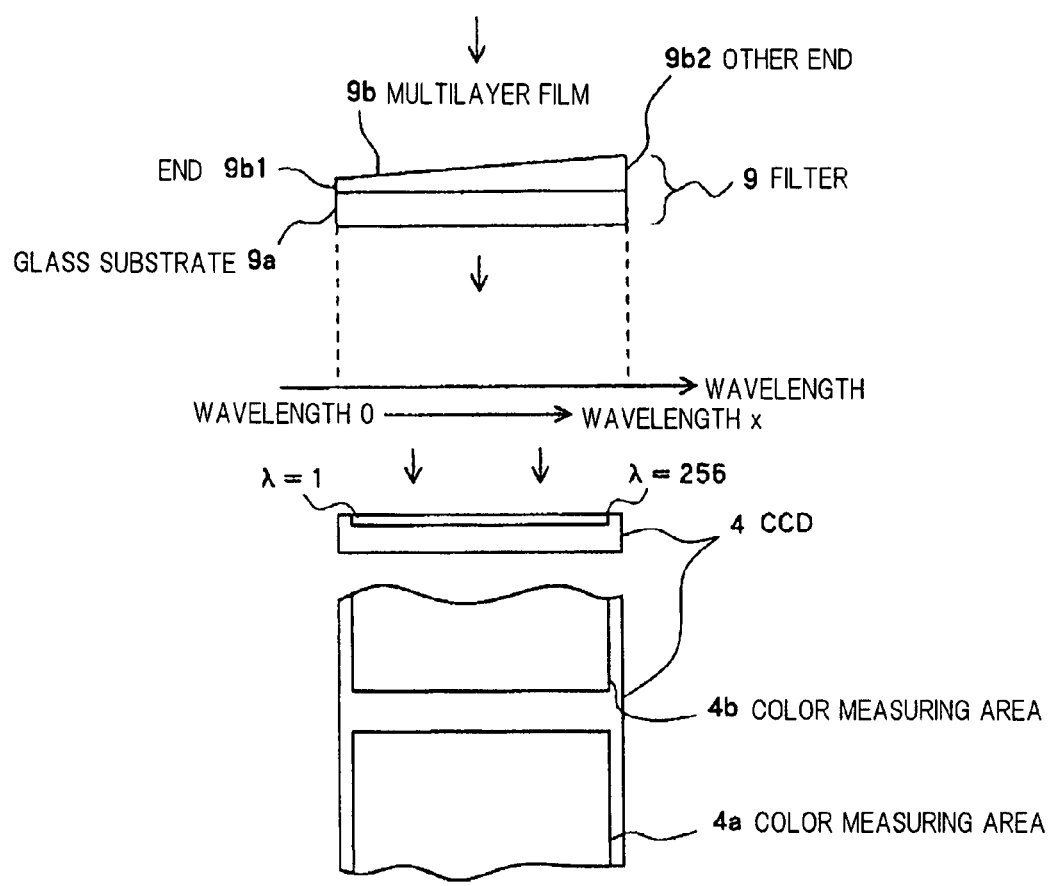
FIG. 5 is a view showing a CCD with a linear variable filter (LVF)

FIG. 5 shows a CCD with a linear variable filter (hereinafter referred to as "filter" or "LVF"). Those parts of the CCD shown in FIG. 5 which are identical to those shown in FIG. 1 are denoted by identical reference characters.

As shown in FIG. 5, filter 9 comprises glass substrate 9a and multilayer film 9b disposed on glass substrate 9a. Multilayer film 9b is progressively thicker from end 9b1 to other end 9b2. Therefore, the wavelength of light passing through filter 9 gradually varies from end 9b1 to other end 9b2.

According to the present invention, filter 9 passes light in a wavelength range from 380 to 720 nm. However, filter 9 may pass light in a different wavelength range rather than the wavelength range from 380 to 7-20 nm.

As shown in FIG. 1, CCD signal processor 6 converts an analog output signal from CCD 4 into a digital signal.

Controller 7 identifies the colors of reaction surfaces 10a through 10c corresponding respectively to color measuring areas 4a through 4c based on the output signals from color measuring areas 4a through 4c. Specifically, controller 7 identifies the color of reaction surface 10a based on the output signal from color measuring area 4a, the color of reaction surface 10b based on the output signal from color measuring area 4b, and the color of reaction surface 10c based on the output signal from color measuring area 4c.

Controller 7 also identifies the gas to be identified based on the output signals from color measuring areas 4a through 4c which correspond respectively to reaction surfaces 10a through 10c.

As described above, controller 7 comprises color information storage unit 7a, gas information storage unit 7b, memory 7c, and processor 7d.

Color information storage unit 7a stores color feature information representing features of colors and color identifying information for identifying colors having features represented by the color feature information, in association with each other.

Gas information storage unit 7b stores gas identifying information for identifying gases and color information about the colors of chemical reagents, which have chemically reacted with gas identified by the gas identifying information, in association with each other.

Memory 7c stores the output signals from color measuring areas 4a through 4c.

Figure 6:
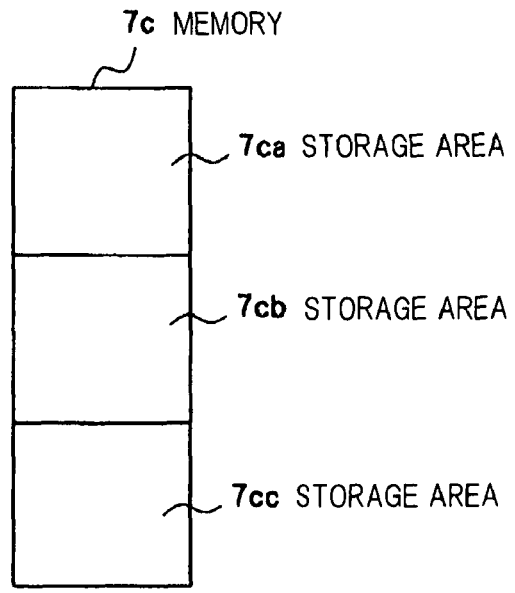
FIG. 6 is a view showing a memory of the gas identifying device shown in FIG. 1.

FIG. 6 shows memory 7c by way of example. As shown in FIG. 6, memory 7c has a plurality of storage areas 7ca, 7cb and 7cc.

Processor 7d shown in FIG. 1 stores the output signal of color measuring area 4a in storage area 7ca, the output signal of color measuring area 4b in storage area 7cb, and the output signal of color measuring area 4c in storage area 7cc.

Processor 7d generates color feature information representing the features of the colors of reaction surfaces 10a through 10c based on the output signals from color measuring areas 4a through 4c which correspond to respective reaction surfaces 10a through 10c. Processor 7d reads the color identifying information associated with the generated color feature information from color information storage unit 7a. Processor 7d then outputs the color identifying information as representing the colors of reaction surfaces 10a through 10c to display unit 8.

Processor 7d also generate color information about the colors of reaction surfaces 10a through 10c based on the output signals from color measuring areas 4a through 4c which correspond to respective reaction surfaces 10a through 10c. Processor 7d identifies color information representing a most similar color to the color identified by the generated color information from the color information stored in gas information storage unit 7b, for the every generated color information. Processor 7d reads the gas identifying information associated with the identified color information from gas information storage unit 7b. Processor 7d outputs the read gas identifying information as representing the gas to be identified to display unit 8.

Display unit 8 displays the information received from processor 7*d*.

Operation of gas identifying device 1000 will be described below with reference to FIG. 7 which is a flowchart of an operation sequence of gas identifying device 1000.

The user inserts reactive board 10 through insertion slot 1*a* into mount block 1 until reactive board 10 is held in place by holder 1*b*.

Then, the user presses buttons 1*c* through 1*h* to crush ampules 102 on reactive board 10. As a result, chemical reagents 101 in ampules 102 are discharged and brought into contact with the gas to be identified on reaction surfaces 10*a* through 10*c*.

Figure 7:
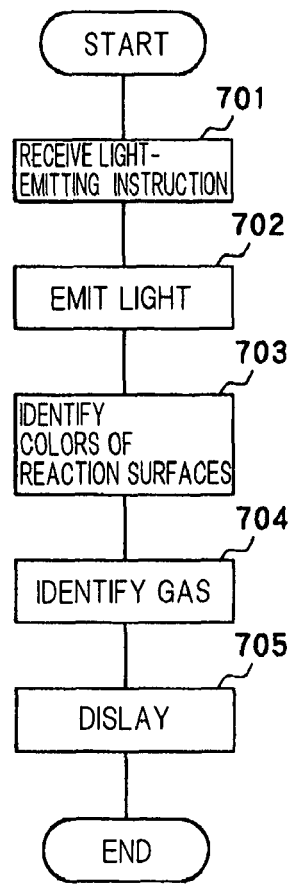
FIG. 7 is a flowchart of an operation sequence of the gas identifying device shown in FIG. 1.

The user enters a light-emitting instruction into input unit 2, which executes step 701 shown in FIG. 7.

In step 701, input unit 2 receives the light-emitting instruction and supplies the light-emitting instruction to light-emitting unit 3 and processor 7. When light-emitting unit 3 receives the light-emitting instruction, it executes step 702.

In step 702, light-emitting unit 3 applies light to reactive board 10.

Reaction surfaces 10*a* through 10*c* of reactive board 10 reflect the light applied by light-emitting unit 3. The reflected light takes on the color (reflected intensity) of chemical reagent 101 which has reacted with the gas to be identified. More specifically, the reflected light takes on the color (reflected intensity) of medium 103 including chemical reagent 101 which has reacted with the gas to be identified.

Lens 5 forms respective images of reaction surfaces 10*a* through 10*c* of reactive board 10 mounted in mount block 1 respectively on color measuring areas 4*a* through 4*c* which correspond to respective reaction surfaces 10*a* through 10*c*.

CCD signal processor 6 converts analog output signals from color measuring areas 4*a* through 4*c*, i.e., analog output signals from the photodetectors of color measuring areas 4*a* through 4*c*, into digital signals. CCD signal processor 6 transmits the digital signals to processor 7*d*.

When processor 7*d* receives the light-emitting instruction from input unit 2, processor 7*d* executes step 703.

In step 703, processor 7*d* identifies the colors of reaction surfaces 10*a* through 10*c* corresponding to color measuring areas 4*a* through 4*c*, based on the output signals from color measuring areas 4*a* through 4*c*.

Specifically, processor 7*d* stores the output signal from color measuring area 4*a* into storage area 7*ca*, the output signal from color measuring area 4*b* into storage area 7*cb*, and the output signal from color measuring area 4*c* into storage area 7*cc*. Thereafter, processor 7*d* generates color feature information representing the feature of the color of reaction surface 10*a* based on the output signal from color measuring area 4*a* which is stored in storage area 7*ca*. Processor 7*d* reads the color identifying information associated with the color feature information from color information storage unit 7*a*. Processor 7*d* then outputs the read color identifying information as representing the color of reaction surface 10*a* to display unit 8.

Thereafter, processor 7*d* generates color feature information representing the feature of the color of reaction surface 10*b* based on the output signal from color measuring area 4*b* which is stored in storage area 7*cb*. Processor 7*d* reads the color identifying information associated with the color feature information from color information storage unit 7*a*. Processor 7*d* then outputs the read color identifying information as representing the color of reaction surface 10*b* to display unit 8.

Thereafter, processor 7*d* generates color feature information representing the feature of the color of reaction surface 10*c* based on the output signal from color measuring area 4*c* which is stored in storage area 7*cc*. Processor 7*d* reads the color identifying information associated with the color feature information from color information storage unit 7*a*. Processor 7*d* then outputs the read color identifying information as representing the color of reaction surface 10*c* to display unit 8.

After having identified the colors of reaction surfaces 10*a* through 10*c*, processor 7*d* executes step 704.

In step 704, processor 7*d* identifies the gas to be identified based on the output signals from color measuring areas 4*a* through 4*c*.

Specifically, processor 7*d* generates color information about the color of reaction surface 10*a* based on the output signal from color measuring area 4*a* which is stored in storage area 7*ca*. Processor 7*d* identifies color information that represents a color which is most similar to the generated color information from the color information stored in gas information storage unit 7*b*. Processor 7*d* reads the gas identifying information associated with the identified color information from gas information storage unit 7*b*. Processor 7*d* outputs the read gas identifying information as representing the gas to be identified to display unit 8.

Then, processor 7*d* generates color information about the color of reaction surface 10*b* based on the output signal from color measuring area 4*b* which is stored in storage area 7*cb*. Processor 7*d* identifies color information that represents a color which is most similar to the generated color information from the color information stored in gas information storage unit 7*b*. Processor 7*d* reads the gas identifying information associated with the identified color information from gas information storage unit 7*b*. Processor 7*d* outputs the read gas identifying information as representing the gas to be identified to display unit 8.

Then, processor 7*d* generates color information about the color of reaction surface 10*c* based on the output signal from color measuring area 4*c* which is stored in storage area 7*cc*. Processor 7*d* identifies color information that represents a color which is most similar to the generated color information from the color information stored in gas information storage unit 7*b*. Processor 7*d* reads the gas identifying information associated with the identified color information from gas information storage unit 7*b*. Processor 7*d* outputs the read gas identifying information as representing the gas to be identified to display unit 8.

When display unit 8 receives the information from processor 7*d*, display unit 8 executes step 705.

In step 705, display unit 8 displays the colors of reaction surfaces 10*a* through 10*c* and the gas to be identified which has chemically reacted on reaction surfaces 10*a* through 10*c*, based on the information received from processor 7*d*.

According to the present invention, lens 5 forms the respective images of reaction surfaces 10*a* through 10*c* of reactive board 10 mounted in mount block 1 on respective color measuring areas 4*a* through 4*c* corresponding to reaction surfaces 10*a* through 10*c*. Controller 7 identifies the colors of reaction surfaces 10*a* through 10*c* which correspond respectively to color measuring areas 4*a* through 4*c* of CCD 4, based on the output signals from color measuring areas 4*a* through 4*c* corresponding to reaction surfaces 10*a* through 10*c*.

Therefore, when the user places reactive board 10 into mount block 1, the colors of reaction surfaces 10*a* through 10*c* of reactive board 10 are measured. The number of parts of color identifying device 1000 is prevented from increasing in a manner to be commensurate with the number of reaction surfaces.

According to the present invention, controller 7 identifies the gas to be identified based on the output signals from color measuring areas 4a through 4c corresponding to reaction surfaces 10a through 10c.

Therefore, when the user places reactive board 10 into mount block 1, the gas to be identified is identified based on the colors of reaction surfaces 10a through 10c of reactive board 10. The number of parts of color identifying device 1000 is prevented from increasing in a manner to be commensurate with the number of reaction surfaces.

EMBODIMENTS

Specific embodiments of the present invention will be described below.

Figure 8:
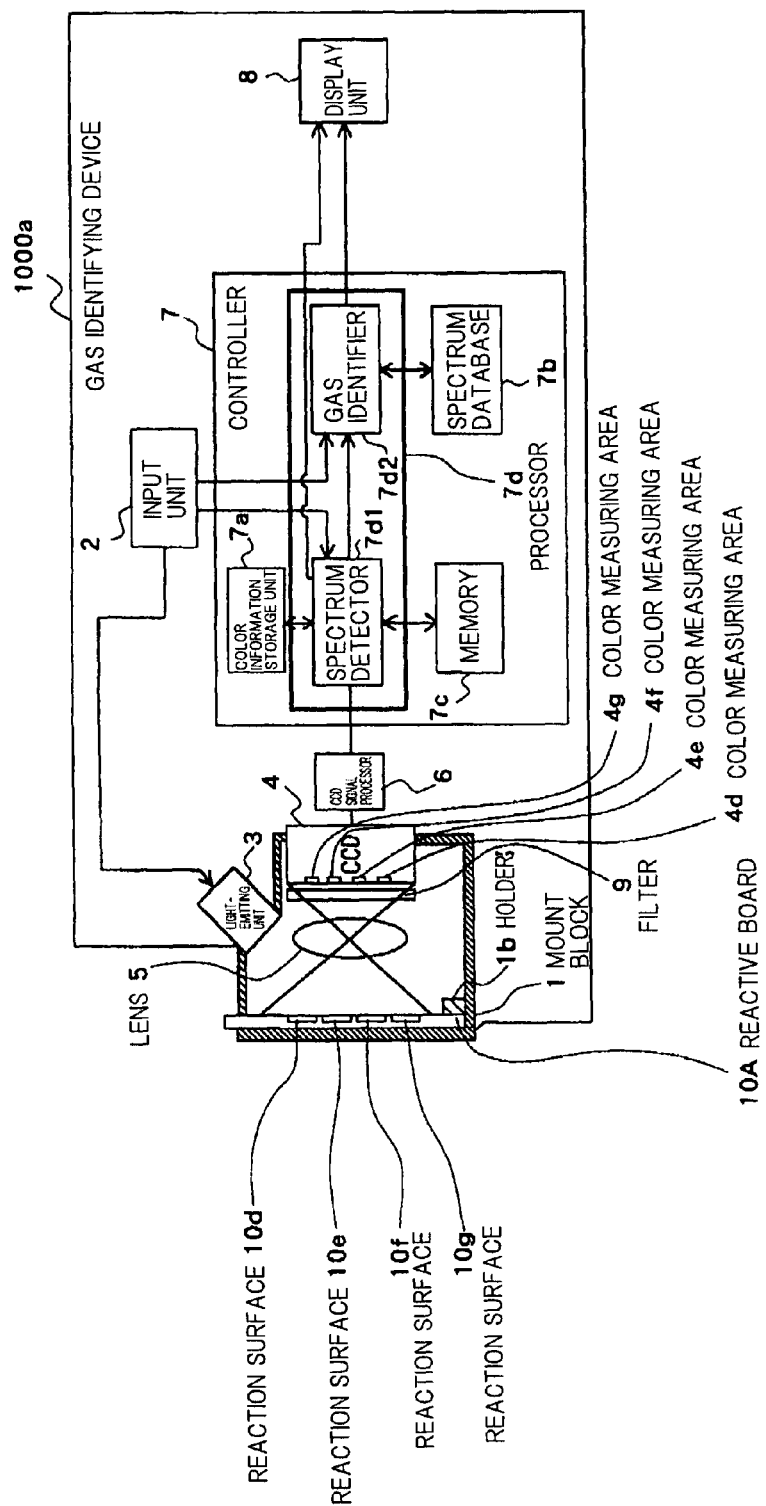
FIG. 8 is a block diagram of a gas identifying device according to a first embodiment of the present invention.

FIG. 8 shows in block form gas identifying device 1000a according to a first embodiment of the present invention. As shown in FIG. 8, gas identifying device 1000a identifies the colors of reaction surfaces and a gas to be identified based on the spectrums of the colors of the reaction surfaces. Those parts of gas identifying device 1000a shown in FIG. 8 which are identical to those shown in FIGS. 1 and 5 are denoted by identical reference characters.

As shown in FIG. 8, gas identifying device 1000a includes mount block 1, input unit 2, light-emitting unit 3, CCD 4, lens 5, CCD signal processor 6, controller 7, display unit 8 and filter 9. Controller 7 comprises color information storage unit 7a, spectrum database 7b as an example of gas information storage unit, memory 7c, and processor 7d. Processor 7d comprises spectrum detector 7d1 and gas identifier 7d2.

Reactive board 10A, which is an example of a board to be measured, is mounted in mount block 1.

Figure 9:
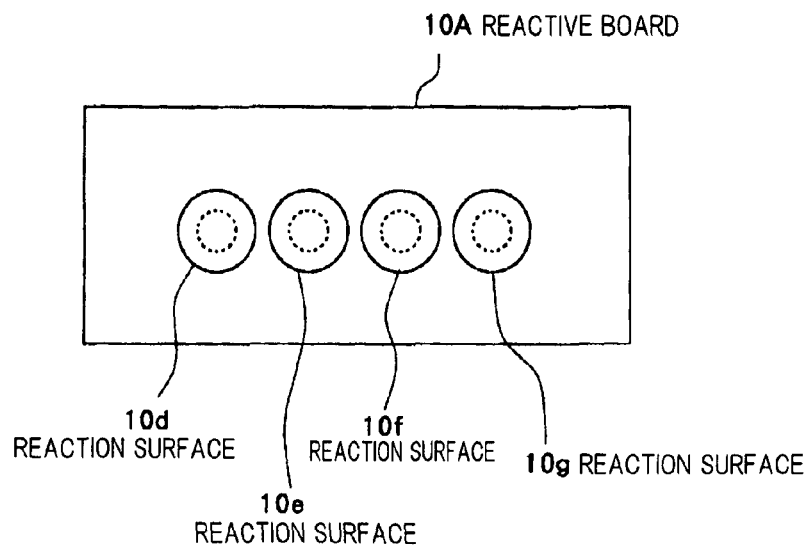
FIG. 9 is a view of a reactive board of the gas identifying device shown in FIG. 8.

FIG. 9 shows reactive board 10A. As shown in FIG. 9, reactive board 10A has a plurality of reaction surfaces (surfaces to be measured) 10d, 10e, 10f, 10g. Each of reaction surfaces 10d, 10e, 10f and 10g is disposed in a predetermined position on reactive board 10A. In FIG. 9, the ampules are omitted from illustration.

For example, each of reaction surfaces 10d, 10e, 10f and 10g has a diameter of 2.5 mm and includes a central area having a diameter of 1.5 mm. Adjacent two of reaction surfaces 10d, 10e, 10f and 10g are spaced from each other by a distance of 0.5 mm. The distance from reaction surface 10d to reaction surface 10g is 11.5 mm.

Figure 10:
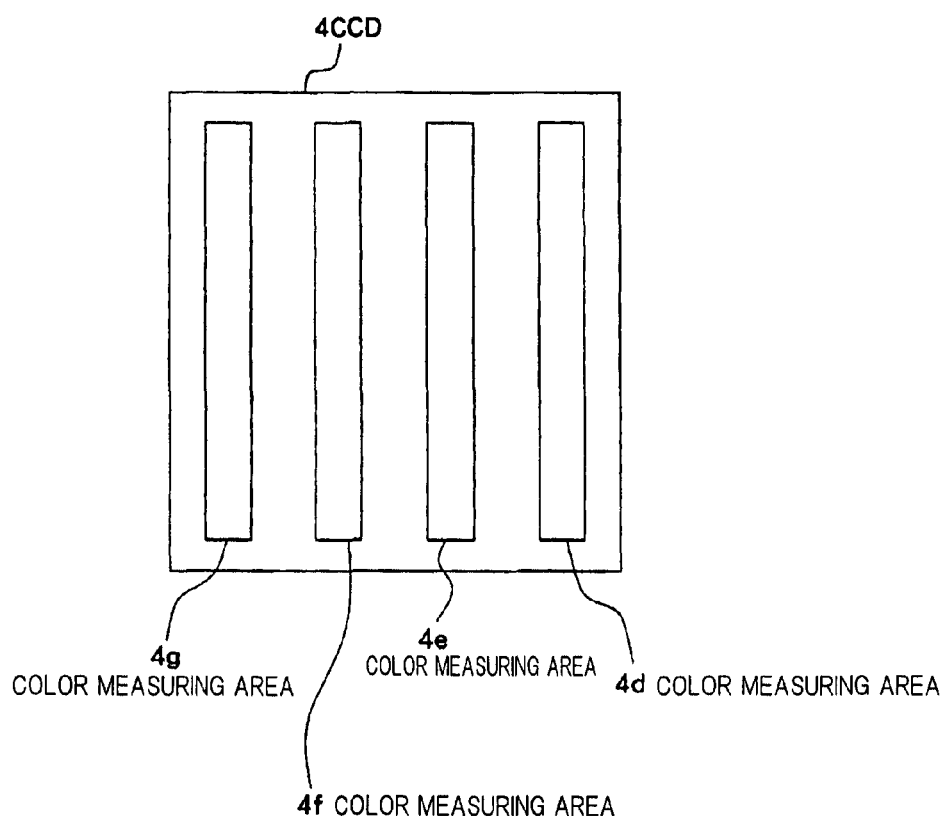
FIG. 10 is a view showing a CCD of the gas identifying device shown in FIG. 8.

FIG. 10 shows CCD 4. As shown in FIG. 10, CCD 4 has a plurality of color measuring areas 4d, 4e, 4f and 4g corresponding respectively to reaction surfaces 10d, 10e, 10f and 10g of reactive board 10A mounted in mount block 1. Specifically, color measuring area 4d corresponds to reaction surface 10d, color measuring area 4e to reaction surface 10e, color measuring area 4f to reaction surface 10f, and color measuring area 4g to reaction surface 10g. Each of color measuring areas 4d, 4e, 4f and 4g comprises an array of photodetectors.

For example, CCD 4 has 512×512 photodetectors (pixels) spaced at a pitch of 24×24 μm. CCD 4 has a chip size of 12.288×12.288 mm. However, CCD 4 is not limited to these details and may have different specifications and dimensions.

For the sake of brevity, it is assumed in the description which follows that each color measuring area of CCD 4 comprises a linear array of 256 photodetectors λ (λ=1 through 256) in the longitudinal direction, i.e., in the vertical direction in FIG. 10.

Figure 11A:
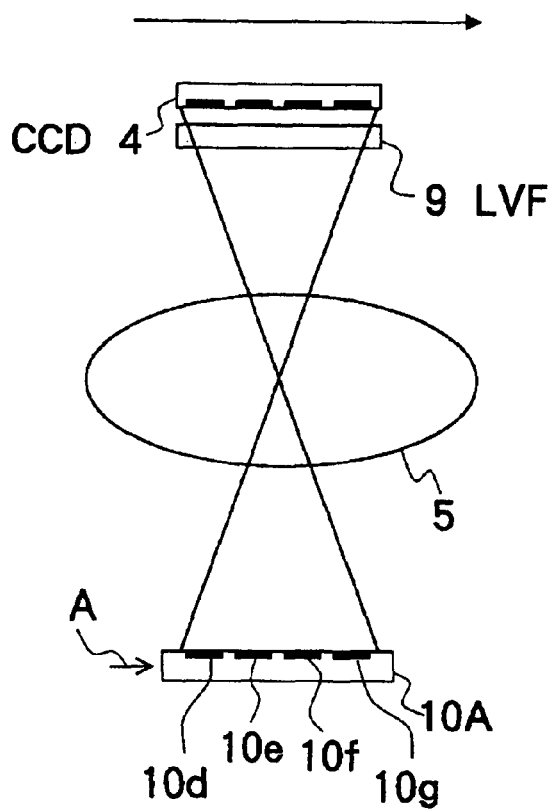
FIGS. 11A and 11B are views showing the relationship of the reactive board mounted in a mount block, a lens, a filter, and the CCD.
Figure 11B:
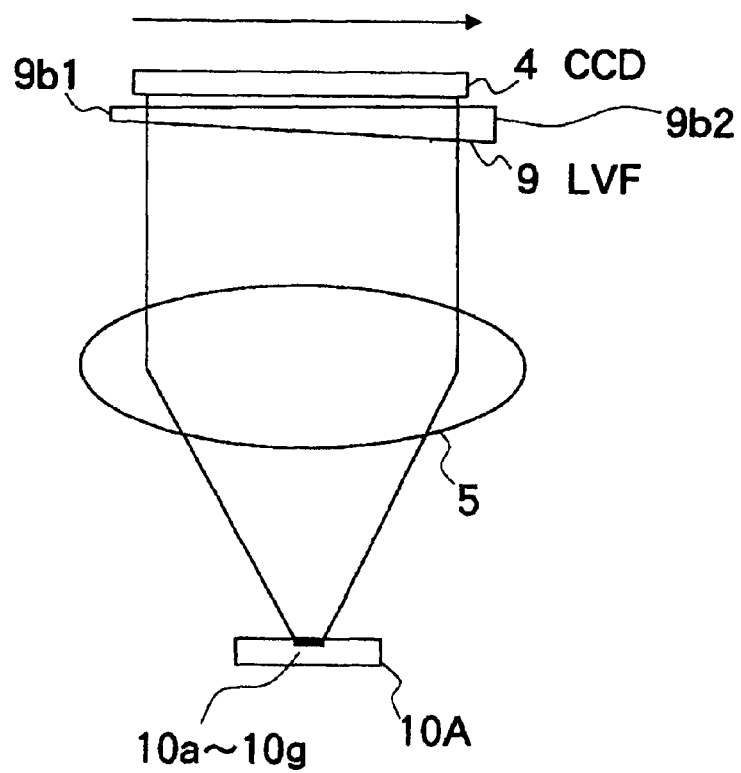

FIGS. 11A and 11B show the relationship of reactive board 10A mounted in mount block 1, lens 5, filter (LVF) 9 and CCD 4. Those parts in FIGS. 11A and 11B which are identical to those shown in FIGS. 8 and 9 are denoted by identical reference characters. FIG. 11B is a view as viewed in the direction of the arrow A in FIG. 11A.

In FIGS. 11A and 11B, lens 5 comprises a cylindrical lens.

As shown in FIG. 11A, cylindrical lens 5 forms the respective images of reaction surfaces 10d-10g through filter (LVF) 9 as unchanged images on CCD 4 in the direction indicated by the arrow A in which reaction surfaces 10d through 10g are arrayed. As shown in FIG. 11B, cylindrical lens 5 forms the respective images of reaction surfaces 10d-10g through filter (LVF) 9 as expanded images on CCD 4 in a direction perpendicular to the direction indicated by the arrow A in which reaction surfaces 10d through 10g are arrayed.

The images expanded by cylindrical lens 5 fall on filter 9. The wavelengths of the images (light rays) that pass through the filter 9 vary gradually from one end 9b1 to other end 9b2 of filter 9.

Figure 12:
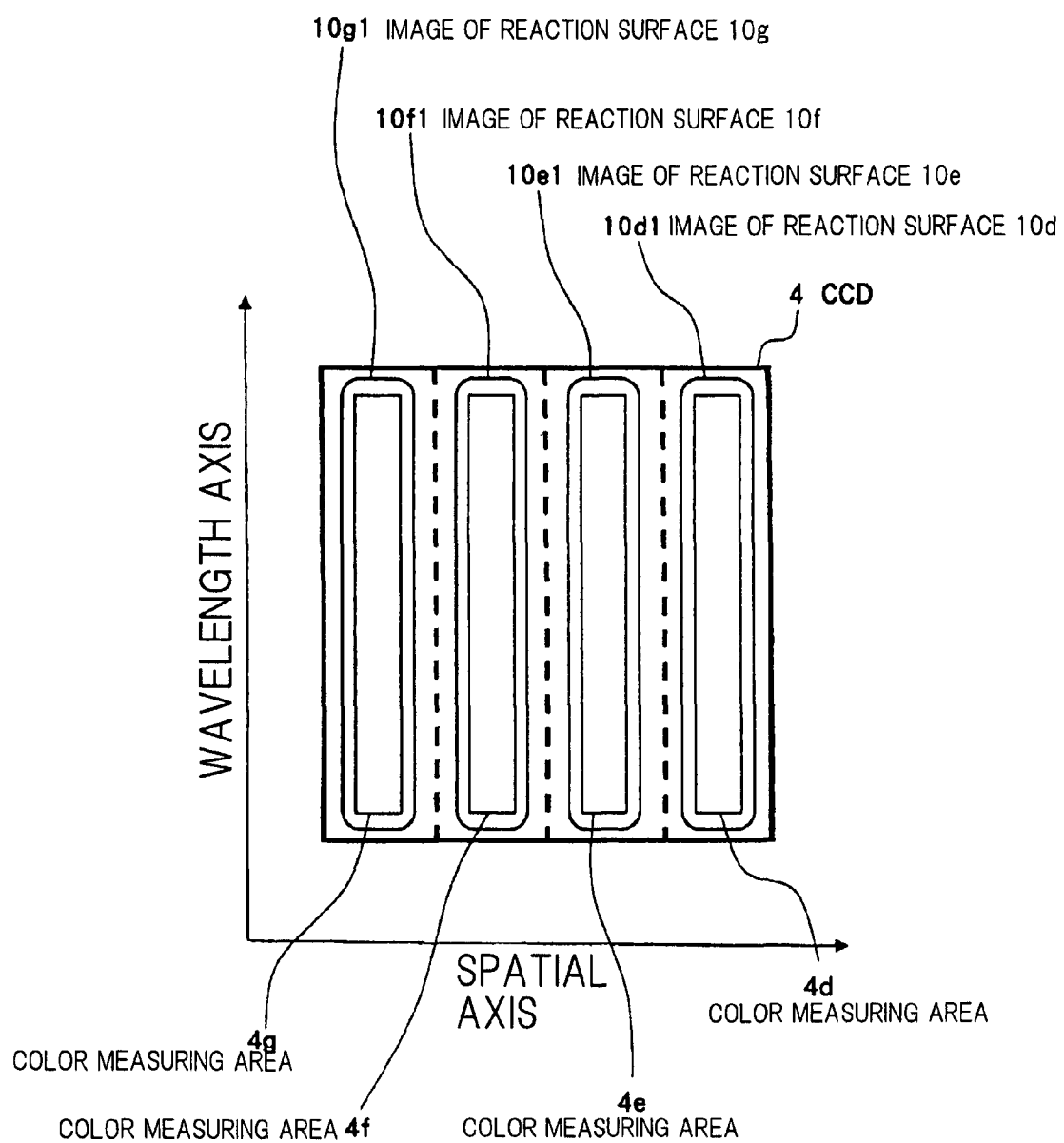
FIG. 12 is a view showing the CCD on which the images of reaction surfaces are formed by the lens.

FIG. 12 shows CCD 4 on which the images of reaction surfaces 10d through 10g are formed by cylindrical lens 5. Those parts shown in FIG. 12 which are identical to those shown in FIG. 10 are denoted by identical reference characters.

As shown in FIG. 12, image 10d1 of reaction surface 10d is formed on color measuring area 4d, image 10e1 of reaction surface 10e on color measuring area 4e, image 10f1 of reaction surface 10f on color measuring area 4f, and image 10g1 of reaction surface 10g on color measuring area 4g.

More specifically, image 10d1 of reaction surface 10d that has passed through filter 9 represents the spectrum of the color of reaction surface 10d. Image 10e1 of reaction surface 10e that has passed through filter 9 represents the spectrum of the color of reaction surface 10e. Image 10f1 of reaction surface 10f that has passed through filter 9 represents the spectrum of the color of reaction surface 10f. Image 10g1 of reaction surface 10g that has passed through filter 9 represents the spectrum of the color of reaction surface 10g.

Therefore, 256 photodetectors λ of color measuring areas 4d through 4g detect light in different wavelengths, and color measuring areas 4d through 4g successively produce output signals depending on the intensities of the light detected by photodetectors λ.

As shown in FIG. 8, input unit 2 receives a dark current measuring instruction, a light-emitting instruction and a binning instruction.

When input unit 2 receives a dark current measuring instruction, input unit 2 supplies the dark current measuring instruction to spectrum detector 7d1. When input unit 2 receives a light-emitting instruction, input unit 2 transmits the light-emitting instruction to light-emitting unit 3 and spectrum detector 7d1.

When input unit 2 receives a binning instruction, input unit 2 transmits the binning instruction to spectrum detector 7d1 and gas identifier 7d2. Instead, a predetermined binning instruction may be set in controller 7.

Color information storage unit 7a stores the names of colors in association with the spectrums of the colors.

Spectrum database 7b stores gas identifying information for identifying gases in association with color information about the colors of chemical reagents that have chemically reacted with gases identified by the gas identifying information.

For example, spectrum database 7b stores color change information as color information. The color change information represents a change from the color of medium 103 before chemical reagent 101 flows into medium 103 to the color of medium 103 after chemical reagent 101 flows into medium 103 and chemically reacts therewith.

In the first embodiment, spectrum database 7b stores spectrum information as color change information. The spectrum information represents a spectrum showing a change of the color of medium 103 which is caused when a gas identified by gas identifying information and chemical reagent 101 chemically react with each other.

In the first embodiment, spectrum database 7b stores color information based on an output signal that is produced by CCD 4 when CCD 4 detects the color of chemical reagent 101 (medium 103) which has chemically reacted with a gas identified by gas identifying information.

FIG. 13 shows an example of data stored in spectrum database 7b.

As shown in FIG. 13, spectrum database 7b stores chemical reagent names 7b1, gas identifying information 7b2 and color information 7b3 in association with each other.

In spectrum database 7b, for example, chemical reagent "A", gas identifying information "a" and the spectrum of the color of chemical reagent "A" which has chemically reacted with a gas represented by gas identifying information "a" (specifically, a color change of medium 103) are associated with each other.

As shown in FIG. 8, spectrum detector 7d1 detects spectrums representing color changes of reaction surfaces 10d through 10g based on an output signal from CCD signal processor 6.

Memory 7c stores the spectrums representing color changes of reaction surfaces 10d through 10g which are detected by spectrum detector 7d1.

Figure 14:
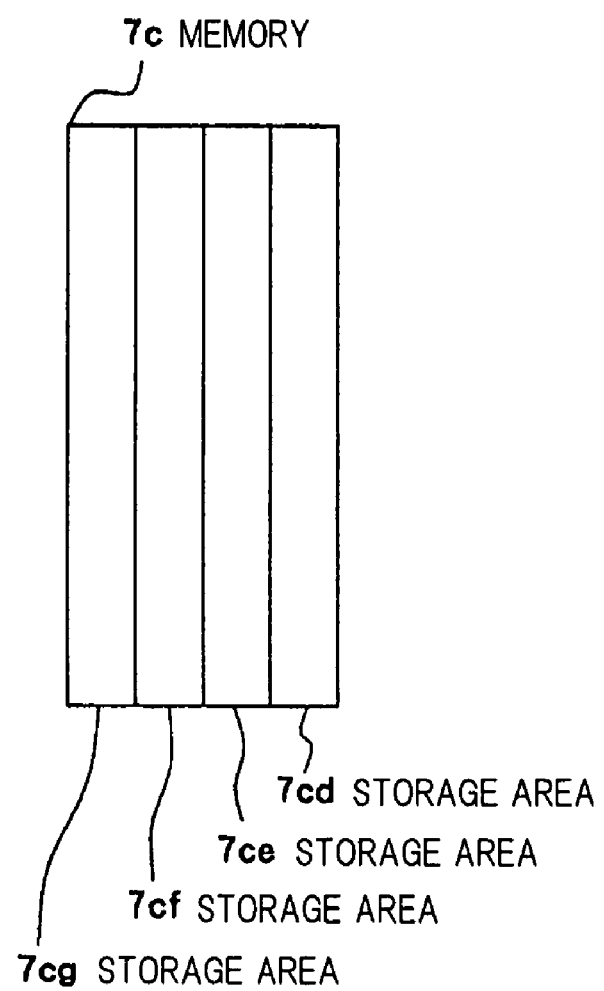
FIG. 14 is a view showing a memory of the gas identifying device shown in FIG. 8.

FIG. 14 shows memory 7c by way of example. As shown in FIG. 14, memory 7c has a plurality of storage areas 7cd, 7ce, 7cf and 7cg. Storage area 7cd corresponds to reaction surface 10d and color measuring area 4d. Storage area 7ce corresponds to reaction surface 10e and color measuring area 4e. Storage area 7cf corresponds to reaction surface 10f and color measuring area 4f. Storage area 7cg corresponds to reaction surface 10g and color measuring area 4g.

Storage area 7cd stores an output signal from color measuring area 4d. Storage area 7ce stores an output signal from color measuring area 4e. Storage area 7cf stores an output signal from color measuring area 4f. Storage area 7cg stores an output signal from color measuring area 4g.

FIG. 15 shows by way of example spectrums representative of color changes of reaction surface 10d which are stored in storage area 7cd. Spectrums representative of color changes of other reaction surfaces 7ce, 7cf and 7cg are stored in other storage areas 7ce, 7cf and 7cg.

In FIG. 15, storage area 7cd stores the names of the photodetectors (λ) of color measuring area 4d corresponding to reaction surface 10d, output values S0, S1, SX thereof, relative intensity (spectral data) S, binning relative intensity (spectral data) Sb, and band value Λ, in association with each other.

Output values S0, S1, SX, relative intensity $\underline{S}$, binning relative intensity Sb, and band value Λ shown in FIG. 15 will be described below. A processing sequence with respect to reaction surface 10d, color measuring area 4d and storage area 7cd only will be described below. A similar processing sequence is also performed with respect to other reaction surfaces, other color measuring areas, and other storage areas.

When input unit 2 receives a dark current measuring instruction before chemical reagent 101 flows into medium 103, input unit 2 supplies the dark current measuring instruction to spectrum detector 7d1.

When spectrum detector 7d1 receives the dark current measuring instruction from input unit 2, spectrum detector 7d1 measures output values $\underline{S0(\lambda)}$ of the photodetectors (λ) of color measuring area 4d at the time light-emitting unit 3 is not energized. Spectrum detector 7d1 stores measured output values $\underline{S0(\lambda)}$ into $\underline{S0}$ in storage area 7cd.

Then, when input unit 2 receives a light-emitting instruction before chemical reagent 101 flows into medium 103, input unit 2 supplies the light-emitting instruction to light-emitting unit 3 and spectrum detector 7d1.

When light-emitting unit 3 receives the light-emitting instruction from input unit 2, light-emitting unit 3 applies light to reactive board 10A.

Reaction surface 10d of reactive board 10A reflects the light applied from light-emitting unit 3. The reflected light takes on the color (reflected intensity) of reaction surface 10d before chemical reagent 101 flows into reaction surface 10d. The reflected light passes through filter 9 and is detected by photodetectors λ of color measuring area 4d. Therefore, an output signal from color measuring area 4d represents the spectrum of the reflected light.

When spectrum detector 7d1 receives the light-emitting instruction after it has received the dark current measuring instruction, spectrum detector 7d1 measures output signals from photodetectors λ of color measuring area 4d, i.e., output values S1 (λ) representing the spectrum of the color of reaction surface 10d before chemical reagent 101 flows into reaction surface 10d. Spectrum detector 7d1 stores output values S1 (λ) into S1 in storage area 7cd.

Thereafter, when ampule 102 on reactive board 10A are crushed, chemical reagent 101 contained in ampule 102 flows into reaction surface 10d. When chemical reagent 101 flows into reaction surface 10d, chemical reagent 101 chemically reacts with the gas to be identified which is held in contact with reaction surface 10d.

When input unit 2 receives a light-emitting instruction again after chemical reagent 101 has flowed into medium 103, input unit 2 supplies the light-emitting instruction to light-emitting unit 3 and spectrum detector 7d1.

When light-emitting unit 3 receives the light-emitting instruction from input unit 2, light-emitting unit 3 emits and applies light to reactive board 10A.

Reaction surface 10d reflects the light applied from light-emitting unit 3. The reflected light takes on the color (reflected intensity) of chemical reagent 101 which has chemically reacted with the gas to be identified. Specifically, the reflected light takes on the color (reflected intensity) of reaction surface 10d including chemical reagent 101 which has chemically reacted with the gas to be identified.

The reflected light passes through filter 9 and is detected by photodetectors λ of color measuring area 4d. Therefore, an output signal from color measuring area 4d represents the spectrum of the reflected light.

When spectrum detector 7d1 receives the light-emitting instruction again from input unit 2, spectrum detector 7d1 measures output signals from photodetectors λ of color measuring area 4d, i.e., output values SX(λ) representing the spectrum of the color of reaction surface 10d after chemical reagent 101 has flowed into reaction surface 10d and has chemically reacted with the gas to be identified. Spectrum detector 7d1 stores output values SX(λ) into SX in storage area 7cd.

After having stored output values SX(λ) into SX in storage area 7cd, spectrum detector 7d1 calculates relative intensity (S(λ)) according to the following equation:

$$S(\lambda)=(SX(\lambda)-S0(\lambda))/(S1(\lambda)-S0(\lambda))$$

If medium 103 has a stable quality, then output values S0(λ) and output values S1 (λ) are measured once, and measured output values S0(λ) and measured output values S1(λ)

may be used in subsequent cycles. This makes it possible to minimize the process of calculating output values $S(\lambda)$.

Spectrum detector 7*d*1 stores output values $S(\lambda)$ into S in storage area 7*cd*.

For storing color information into spectrum database 7*b*, the same process as described above is performed while the gas identified by the gas identifying information is being held in contact with medium 103. Calculated output values $S(\lambda)$ are stored into spectrum database 7*b* as color information associated with the gas identifying information.

After having stored output values $S(\lambda)$ in storage area 7*cd*, spectrum detector 7*d*1 calculates binning relative intensity (spectral data) $Sb(\Lambda)$ based on a binning instruction supplied from input unit 2.

For example, if a binning instruction "4" is supplied from input unit 2, then spectrum detector 7*d*1 calculates binning relative intensity $Sb(\Lambda)$ based on a cluster of four output values $S(\lambda)$. In the example shown in FIG. 15, the sum of four output values $S(1)$ through $S(4)$ becomes binning relative intensity $Sb(\Lambda=1)$, and the sum of four output values $S(253)$ through $S(256)$ becomes binning relative intensity $Sb(\Lambda=64)$.

Spectrum detector 7*d*1 stores calculated binning relative intensities $Sb(\Lambda)$ into $Sb(\Lambda)$ in storage area 7*cd*. Thereafter, spectrum detector 7*d*1 supplies binning relative intensities $Sb(\Lambda)$ to gas identifier 7*d*2.

When spectrum detector 7*d*1 receives the binning instruction from input unit 2, spectrum detector 7*d*1 calculates band ($\Lambda$) based on the binning instruction, and stores calculated band ($\Lambda$) into $\Lambda$ in storage area 7*cd*.

Gas identifier 7*d*2 identifies spectrum information representing a spectrum which is most similar to the spectrum representing the color change of reaction surface 10*d* detected by spectrum detector 7*d*1, from the spectrum information 7*b*3 stored in spectrum database 7*b*.

According to the first embodiment, gas identifier 7*d*2 identifies spectrum information which satisfies the two conditions 1 and 2 described below from spectrum information 7*b*3 stored in spectrum database 7*b*.

Condition 1: spectrum information having a spectrum waveform which is most similar to the waveform of the spectrum that represents the color change of the reaction surface.

Condition 2: spectrum information having a spectrum waveform whose coincidence with the waveform of the spectrum that represents the color change of the reaction surface is equal to or greater than a predetermined value.

Specifically, gas identifier 7*d*2 performs the following process:

Gas identifier 7*d*2 hypothetically places spectrum $Sb(\Lambda)$ that represents the color change of the reaction surface which is detected by spectrum detector 7*d*1, in a multidimensional space having coordinates A. Thus, spectrum $Sb(\Lambda)$ is indicated as a vector in the multidimensional space.

Gas identifier 7*d*2 processes each of the spectrum information stored in spectrum database 7*b* based on the binning instruction supplied from input unit 2 to equalize the number of bands of each of the spectrum information to the number of bands of spectrum $Sb(\Lambda)$.

For example, if a binning instruction "4" is supplied from input unit 2, then gas identifier 7*d*2 brings the spectrum information of gases identified by gas identifying information 7*b*2 into clusters of four items of spectrum information to equalize the number of bands of each of the spectrum information stored in spectrum database 7*b* to the number of bands of spectrum $Sb(\Lambda)$.

Gas identifier 7*d*2 hypothetically places each of the spectrum information which has the same number of bands as the number of bands of spectrum $Sb(\Lambda)$, in the multidimensional space having coordinates $\Lambda$, as with spectrum $Sb(\Lambda)$. Thus, each of the spectrum information is indicated as a vector in the multidimensional space.

Gas identifier 7*d*2 calculates the inner product of spectrum $Sb(\Lambda)$ and each of the spectrum information. Based on the calculated inner product, gas identifier 7*d*2 selects the spectrum information whose angle formed with respect to spectrum $Sb(\Lambda)$ is the smallest. This process is known in the art as spectral angle mapper (SAM).

The angle formed between the spectrum information and spectrum $Sb(\Lambda)$ is smaller as their spectral waveforms are closer to each other. Stated otherwise, the angle formed between the spectrum information and spectrum $Sb(\Lambda)$ is representative of the degree of coincidence between the spectrum information and spectrum $Sb(\Lambda)$.

Then, gas identifier 7*d*2 determines whether or not the angle between spectrum $Sb(\Lambda)$ and the selected spectrum information is equal to or smaller than a predetermined angle.

If the angle between spectrum $Sb(\Lambda)$ and the selected spectrum information is equal to or smaller than the predetermined angle, then gas identifier 7*d*2 identifies the selected spectrum information as spectrum information representative of spectrum $Sb(\Lambda)$.

Gas identifier 7*d*2 reads gas identifying information 7*b*2 associated with the identified gas information from spectrum database 7*b*.

Gas identifier 7*d*2 outputs read gas identifying information 7*b*2 as gas identifying information representing the gas to be identified to display unit 8.

Operation of gas identifying device 1000*a* according to the first embodiment will be described below.

Figure 16:
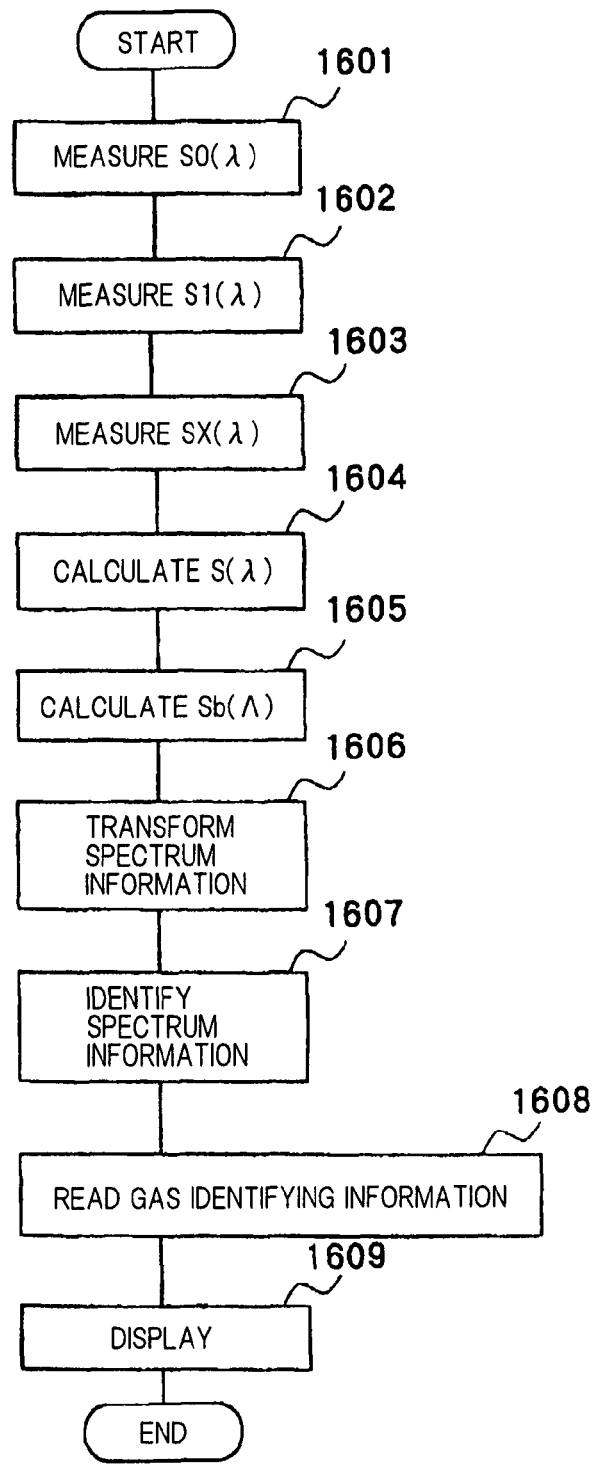
FIG. 16 is a flowchart of an operation sequence of the gas identifying device shown in FIG. 8.

FIG. 16 is a flowchart of an operation sequence of gas identifying device 1000*a*. Operation of gas identifying device 1000*a* will be described below with reference to FIG. 16.

It is assumed that the user has entered a binning instruction "binning=4" to input unit 2. The binning instruction is not limited to "binning 4", but may be of any of binning values.

The user inserts reactive board 10A through insertion slot 1*a* into mount block 1 until reactive board 10A is held in place by holder 1*b*. At this time, the ampules on reactive board 10A have not been crushed yet. When reactive board 10A is inserted into mount block 1, external light should not enter mount block 1.

Then, the user enters a dark current measuring instruction into input unit 2. When input unit 2 receives the dark current measuring instruction, step 1601 is executed.

In step 1601, the following process is performed:

Input unit 2 supplies the dark current measuring instruction to spectrum detector 7*d*1.

When spectrum detector 7*d*1 receives the dark current measuring instruction, spectrum detector 7*d*1 measures output values $S0(\lambda)$ of photodetectors $\lambda$ of color measuring areas 4*d* through 4*g* when light-emitting unit 3 does not emit light.

Spectrum detector 7*d*1 stores measured output values $S0(\lambda)$ into S0 in storage areas 7*cd*, 7*ce*, 7*cf* and 7*cg* (memory 7*c*) which correspond respectively to color measuring areas 4*d* through 4*g*.

The process in step 1601 is now finished.

Then, the user enters a light-emitting instruction into input unit 2. When input unit 2 receives the light-emitting instruction, step 1602 is executed.

In step 1602, the following process is performed:

Input unit 2 supplies the light-emitting instruction to light-emitting unit 3 and spectrum detector 7*d*1.

When light-emitting unit 3 receives the light-emitting instruction, light-emitting unit 3 applies light to reactive board 10A.

Reaction surfaces 10d through 10g of reactive board 10A reflect the light applied from light-emitting unit 3. The reflected light takes on the colors (reflected intensities) of reaction surfaces 10d through 10g before chemical reagents 101 flow into reaction surfaces 10d through 10g. The reflected light passes through filter 9 and is detected by photodetectors λ of color measuring areas 4d through 4g. Therefore, output signals from color measuring areas 4d through 4g represent the spectrums of the reflected light which correspond to color measuring areas 4d through 4g.

When spectrum detector 7d1 receives the light-emitting instruction after it has received the dark current measuring instruction, spectrum detector 7d1 measures output signals from photodetectors λ of color measuring areas 4d through 4g, i.e., output values S1 (λ) representing the spectrums of the colors of reaction surfaces 10d through 10g before chemical reagents 101 flow into reaction surfaces 10d through 10g. Spectrum detector 7d1 stores output values S1 (λ) into S1 in storage areas 7cd through 7cg(memory 7c) which correspond to color measuring areas 4d through 4g.

The process in step 1602 is now finished.

Then, the user presses buttons, not shown, on mount block 1 to crush ampules 102 on reactive board 10A.

When ampules 102 are crushed, chemical reagents 101 contained in ampules 102 are discharged and flow into reaction surfaces 10d through 10g. When chemical reagents 101 flow into reaction surfaces 10d through 10g, they chemically react the gas to be identified which is held in contact with mediums 103.

Then, the user enters a light-emitting instruction again into input unit 2. When input unit 2 receives the light-emitting instruction again, step 1603 is executed.

In step 1603, the following process is performed:

Input unit 2 supplies the light-emitting instruction to light-emitting unit 3 and spectrum detector 7d1.

When light-emitting unit 3 receives the light-emitting instruction, light-emitting unit 3 applies light to reactive board 10A.

Reaction surfaces 10d through 10g of reactive board 10A reflect the light applied from light-emitting unit 3. The reflected light takes on the colors (reflected intensities) of chemical reagents 101 which have chemically reacted with the gas to be identified. Specifically, the reflected light takes on the colors of reaction surfaces 10d through 10g containing chemical reagents 101 which have chemically reacted with the gas to be identified.

The reflected light passes through filter 9 and is detected by photodetectors λ of color measuring areas 4d through 4g. Therefore, output signals from color measuring areas 4d through 4g represent the spectrums of the reflected light from reactive surfaces 10d through 10g which correspond to color measuring areas 4d through 4g.

When spectrum detector 7d1 receives the light-emitting instruction again from input unit 2, spectrum detector 7d1 measures output signals from photodetectors λ of color measuring areas 4d through 4g, i.e., output values SX(λ) representing the spectrums of the colors of reaction surfaces 10d through 10g after chemical reagents 101 have flowed into reaction surfaces 10d through 10g. Spectrum detector 7d1 stores output values SX(λ) into SX in storage areas 7cd through 7cg (memory 7c) which correspond to color measuring areas 4d through 4g.

The process in step 1603 is now finished.

After having stored output values SX(λ) into memory 7c, spectrum detector 7d1 executes step 1604.

In step 1604, spectrum detector 7d1 calculates relative intensities S(λ) with respect to the respective output values of color measuring areas 4d through 4g which are stored in respective storage areas 7cd through 7cg according to the following equation:

$$S(\lambda)=(SX(\lambda)-S0(\lambda))/(S1(\lambda)-S0(\lambda))$$

Spectrum detector 7d1 stores calculated relative intensities S(λ) into S in storage areas 7cd through 7cg (memory 7c) corresponding to relative intensities S(λ). After having stored calculated relative intensities S(λ) into memory 7c, spectrum detector 7d1 executes step 1605.

In step 1605, spectrum detector 7d1 calculates binning relative intensities (spectral data) Sb(Λ) with respect to the output values of color measuring areas 4d through 4g which are stored in storage areas 7cd through 7cg, based on a binning instruction supplied from input unit 2.

Since a binning instruction "4" is supplied from input unit 2, spectrum detector 7d1 calculates binning relative intensities Sb(Λ) for respective clusters of four relative intensities S(λ).

Spectrum detector 7d1 stores calculated binning relative intensities Sb(Λ) into Sb(Λ) in storage areas 7cd through 7cg corresponding to relative intensities S(Λ). Thereafter, spectrum detector 7d1 supplies binning relative intensities Sb(Λ) to gas identifier 7d2.

When gas identifier 7d2 receives binning relative intensities Sb(Λ), gas identifier 7d2 executes steps 1606 and 1607 using SAM.

In steps 1606 and 1607, gas identifier 7d2 identifies the spectrum information which satisfies two conditions 1 and 2 described below from spectrum information 7b3 stored in spectrum database 7b, with respect to respective output values of color measuring areas 4d through 4g which are stored in respective storage areas 7cd through 7cg.

Condition 1: spectrum information having a spectrum waveform which is most similar to the waveform of the spectrum that represents the color change of the reaction surface which is detected by spectrum detector 7d1.

Condition 2: spectrum information having a spectrum waveform whose coincidence with the waveform of the spectrum that represents the color change of the reaction surface is equal to or greater than a predetermined value.

Specifically, gas identifier 7d2 performs the following process:

Gas identifier 7d2 executes step 1606.

In step 1606, gas identifier 7d2 performs the following process on each of the data of color measuring areas 4d through 4g:

Gas identifier 7d2 hypothetically places spectrum Sb(Λ) that represents the color change of the reaction surface which is detected by spectrum detector 7d1, in a multidimensional space having coordinates Λ.

Gas identifier 7d2 processes each of the spectrum information stored in spectrum database 7b based on the binning instruction supplied from input unit 2 to equalize the number of bands of each of the spectrum information to the number of bands of spectrum Sb(Λ).

Since a binning instruction "4" is supplied from input unit 2, gas identifier 7d2 brings the spectrum information of gases identified by gas identifying information 7b2 into clusters of four items of spectrum information to equalize the number of bands of each of the spectrum information stored in spectrum database 7b to the number of bands of spectrum Sb(Λ).

Gas identifier 7d2 hypothetically places each of the spectrum information which has the same number of bands as the number of bands of spectrum Sb(Λ), in the multidimensional space having coordinates Λ, as with spectrum Sb(Λ).

After having hypothetically placed each of the spectrum information in the multidimensional space having coordinates Λ, gas identifier 7d2 executes step 1607.

In step 1607, gas identifier 7d2 calculates the inner product of spectrum Sb(Λ) and each of the spectrum information. Based on the calculated inner product, gas identifier 7d2 selects the spectrum information whose angle formed with respect to spectrum Sb(Λ) is the smallest.

Then, gas identifier 7d2 determines whether or not the angle between spectrum Sb(Λ) and the selected spectrum information is equal to or smaller than a predetermined angle.

If the angle between spectrum Sb(Λ) and the selected spectrum information is equal to or smaller than the predetermined angle, then gas identifier 7d2 identifies the selected spectrum information as spectrum information representative of spectrum Sb(Λ).

Figure 17A:
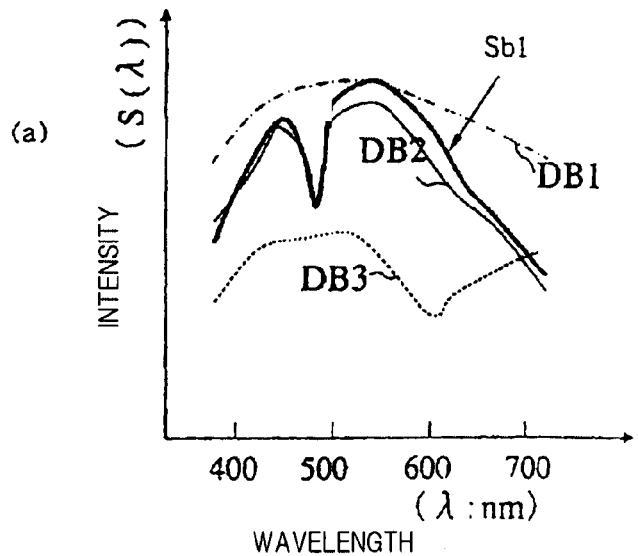
FIG. 17a through 17c are diagrams illustrative of a method of identifying spectral information.
Figure 17B:
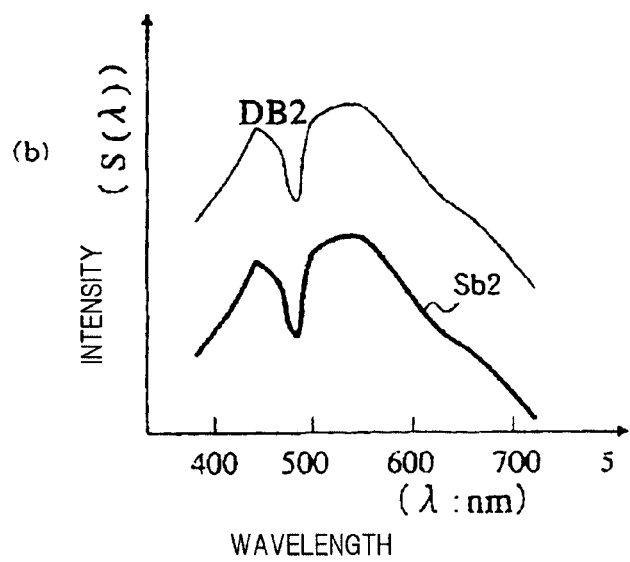
Figure 17C:
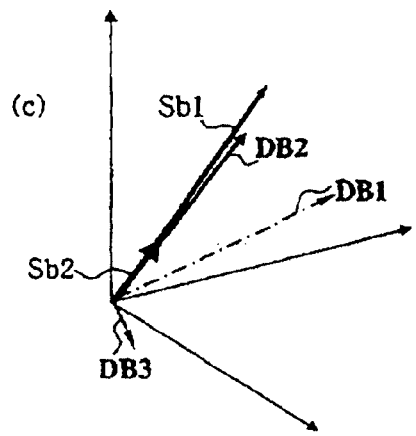

FIGS. 17a through 17c are illustrative of a method of identifying spectral information using SAM.

In FIGS. 17a and 17b, DB1 represents the spectral waveform of spectrum information associated with gas identifying information "a", DB2 the spectral waveform of spectrum information associated with gas identifying information "b", and DB3 the spectral waveform of spectrum information associated with gas identifying information "c".

In FIG. 17a, Sb1 represents a measured spectrum. Measured spectrum Sb1 has a waveform and an intensity similar to spectral waveform DB2. In FIG. 17b, Sb2 represents a measured spectrum. Measured spectrum Sb2 has a waveform which is the same as spectral waveform DB2 and has an intensity which is different from spectral waveform DB2.

The degree of coincidence between spectral waveforms indicates the degree of coincidence between chemical reactions.

However, the degree of coincidence between intensities does not necessarily indicate the degree of coincidence between chemical reactions because the intensity varies depending on the ambient temperature and moisture and the concentration of the gas in chemical reactions.

Therefore, it is desirable to identify spectrum information corresponding to a measured spectrum by determining whether spectral waveforms coincide with each other or not.

According to the first embodiment, spectrum information is identified according to SAM. Consequently, spectrum information corresponding to a measured spectrum is identified based on the degree of coincidence between spectral waveforms.

FIG. 17c is illustrative of an example in which DB1, DB2, DB3, Sb1 and Sb2 are placed in one multidimensional space.

As shown in FIG. 17c, the angle between similar spectral waveforms Sb1 and DB2 is small, and the angle between similar spectral waveforms Sb2 and DB2 is also small.

According to the first embodiment, therefore, not only if spectral waveforms and intensities are similar to each other as shown in FIG. 17a, but also if spectral waveforms are similar to each other, but spectral intensities are different from each other, it is possible to identify spectrum information corresponding to a measured spectrum.

After having specified spectrum information representative of spectrum Sb(Λ), gas identifier 7d2 executes step 1608.

In step 1608, gas identifier 7d2 reads gas identifying information 7b2 associated with the identified spectrum information from spectrum database 7b.

Gas identifier 7d2 outputs read gas identifying information 7b2 to display unit 8.

When display unit 8 receives gas identifying information 7b2 from gas identifier 7d2, display unit 8 executes step 1609.

In step 1609, display unit 8 displays gas identifying information 7b2.

In the present embodiment, processor 7d identifies the color of each reaction surface based on the spectrum of the color of the reaction surface. Therefore, it is possible to identify the color of each reaction surface with high accuracy.

In the present embodiment, processor 7d identifies the gas to be identified which has chemically reacted with the chemical reagents on the reaction surfaces, based on the spectrum of the color of each reaction surface.

Therefore, it is possible to identify the gas to be identified with high accuracy. In the present embodiment, spectrum database 7b and processor 7d may be modified as follows:

Spectrum database 7b stores gas identifying information and absorption lines obtained from the spectrums of the colors of chemical reagents 101 which have chemically reacted with gases identified by the gas identifying information, in association with each other.

Processor 7d identifies the absorption line of a substance that is generated by the chemical reaction between a gas to be identified and chemical reagent 101, based on the color detected in the color measuring area. Processor 7d identifies an absorption line closest to the absorption line from absorption lines stored in spectrum database 7b. Processor 7d reads the gas identifying information associated with the identified absorption line as the gas identifying information representative of the gas to be identified, from spectrum database 7b.

It is thus possible to identify the gas to be identified based on the absorption line of the substance that is generated by the chemical reaction between the gas and the chemical reagent.

Color information may be stored in spectrum database 7b as follows:

The user introduces a plurality of chemical reagents into mediums 103 held in contact with a given gas in a predetermined sequence. Then, the user successively detects changes in the colors of mediums 103 using color measuring areas. Spectrum database 7b stores the color changes that are successively detected by the color measuring areas, as color information corresponding to the given gas (identifying information of the given gas).

Controller 7 identifies a gas to be identified as follows:

The user introduces a plurality of chemical reagents into reaction surfaces held in contact with a gas to be identified in the predetermined sequence, and successively detects changes in the colors of reaction surfaces using the color measuring areas.

Each time a color detecting area detects a change in the color of the reaction surface, processor 7d compares the detected color change with the color information stored in spectrum database 7b, and identifies the color information representing a color that is most similar to the color detected by the color detecting area, from the color information stored in spectrum database 7b. Processor 7d then reads the gas identifying information associated with the identified color information from spectrum database 7b.

The gas identifying device according to the first embodiment may be modified as follows:

CCD 4 detects light emitted from light-emitting unit 3 and transmitted through the reaction surfaces, rather than detecting light emitted from light-emitting unit 3 and reflected by the reaction surfaces.

The gas identifying device may be incorporated in the reader device disclosed in U.S. Pat. No. 6,228,657B1.

Colors may be identified using SAM.

A gas identifying device according to a second embodiment of the present invention will be described below.

Figure 18:
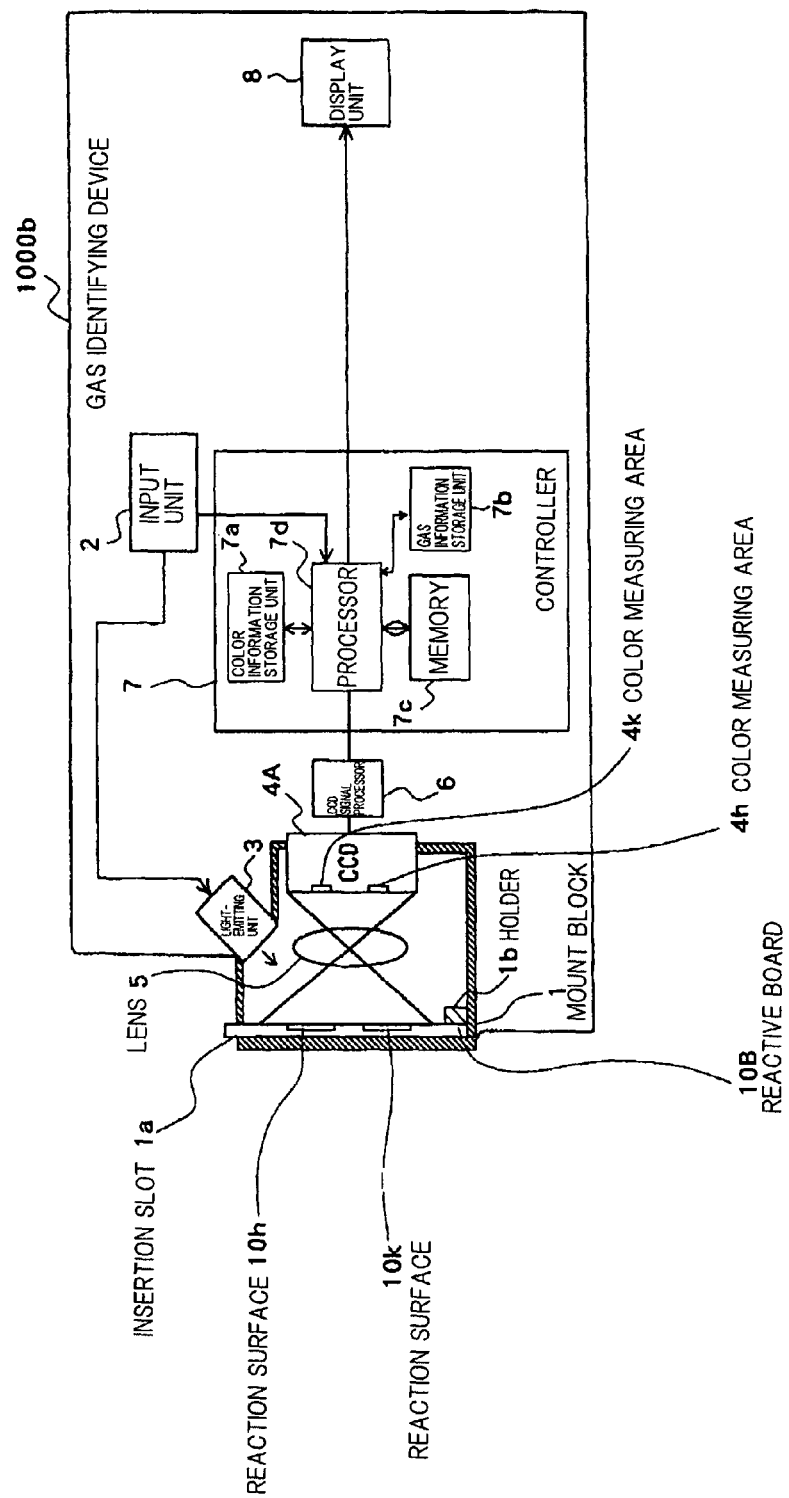
FIG. 18 is a block diagram of a gas identifying device according to a second embodiment of the present invention.

FIG. 18 shows in block form gas identifying device 1000b according to the second embodiment. Gas identifying device 1000b identifies the colors of respective reaction surfaces and a gas to be identified, based on the ratio of components R, G, B of the colors of the reaction surfaces. Those parts of gas identifying device 1000b shown in FIG. 18 which are identical to those shown in FIG. 1 are denoted by identical reference characters.

As shown in FIG. 18, gas identifying device 1000b comprises mount block 1, input unit 2, light-emitting unit 3, color CCD 4A, lens 5, CCD signal processor 6, controller 7 and display unit 8.

Controller 7 comprises color information storage unit 7a, gas information storage unit 7b, memory 7c and processor 7d.

Reactive board 10B, which is an example of a board to be measured, is mounted in mount block 1.

Figure 19:
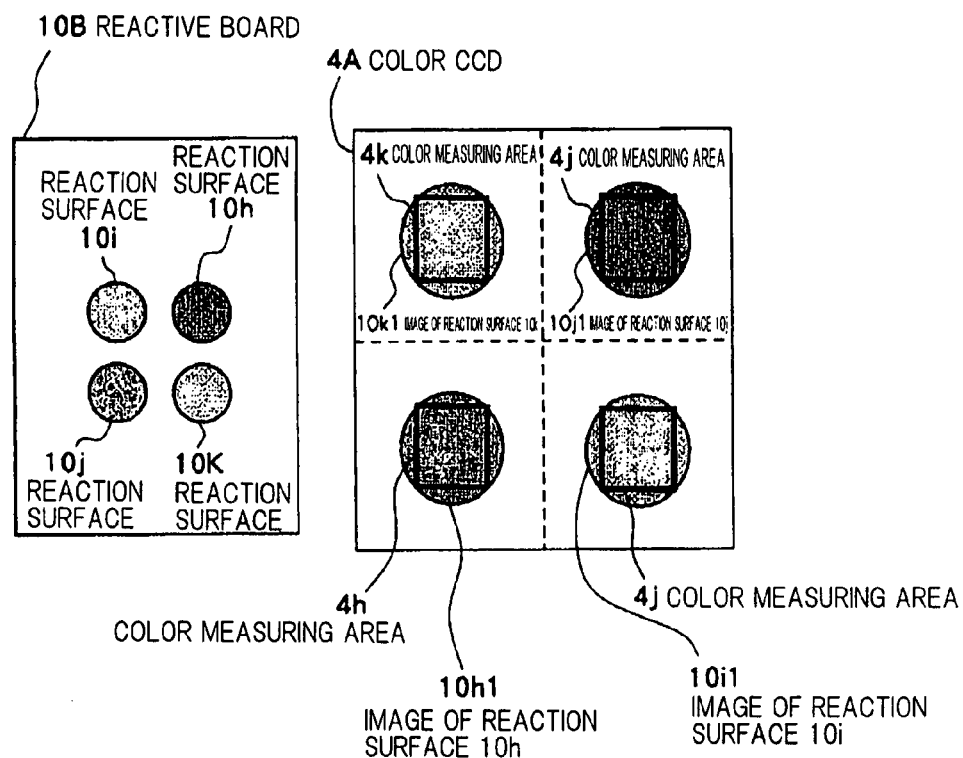
FIG. 19 is a view of a reactive board and a color CCD of the gas identifying device shown in FIG. 18.

FIG. 19 shows reactive board 10B and color CCD 4A.

As shown in FIG. 19, reactive board 10B has a matrix of reaction surfaces (surfaces to be measured) 10h, 10i, 10j and 10k. Each of reaction surfaces 10h through 10k is disposed in a predetermined position on reactive board 10B. In FIG. 19, the ampules are omitted from illustration.

Color CCD 4A has a plurality of color measuring areas 4h, 4i, 4j and 4k corresponding respectively to reaction surfaces 10h, 10i, 10j and 10k of reactive board 10B mounted in mount block 1. Specifically, color measuring area 4h corresponds to reaction surface 10h, color measuring area 4i to reaction surface 10i, color measuring area 4j to reaction surface 10j, and color measuring area 4k to reaction surface 10k. Each of color measuring areas 4h through 4k comprises an array of photodetectors.

When reactive board 10B is mounted in mount block 1 and held by holder 1b, lens 5 forms image 10h1 of reaction surface 10h on color measuring area 4h, image 10i1 of reaction surface 10i on color measuring area 4i, image 10j1 of reaction surface 10j on color measuring area 4j, and image 10k1 of reaction surface 10k on color measuring area 4k at the same time.

Therefore, an output signal from color measuring area 4h varies depending on the color of reaction surface 10h, an output signal from color measuring area 4i varies depending on the color of reaction surface 10i, an output signal from color measuring area 4j varies depending on the color of reaction surface 10j, and an output signal from color measuring area 4k varies depending on the color of reaction surface 10k.

As shown in FIG. 18, color information storage unit 7a stores a chromaticity diagram. The chromaticity diagram has x and y coordinates. The x coordinates represent values $R/(R+G+B)$, and the y coordinates values $G/(R+G+B)$. R represents a red component of color, G a green component of color, and B a blue component of color. The chromaticity diagram is peculiar to the present invention. In other words, the chromaticity diagram may be a relative chromaticity diagram.

Gas information storage unit 7b stores gas identifying information for identifying gases and chromaticity diagram coordinates of the colors of chemical reagents that have chemically reacted with gases identified by the gas identifying information, in association with each other.

Memory 7c stores the output signals from color measuring areas 4h through 4k.

Figure 20:
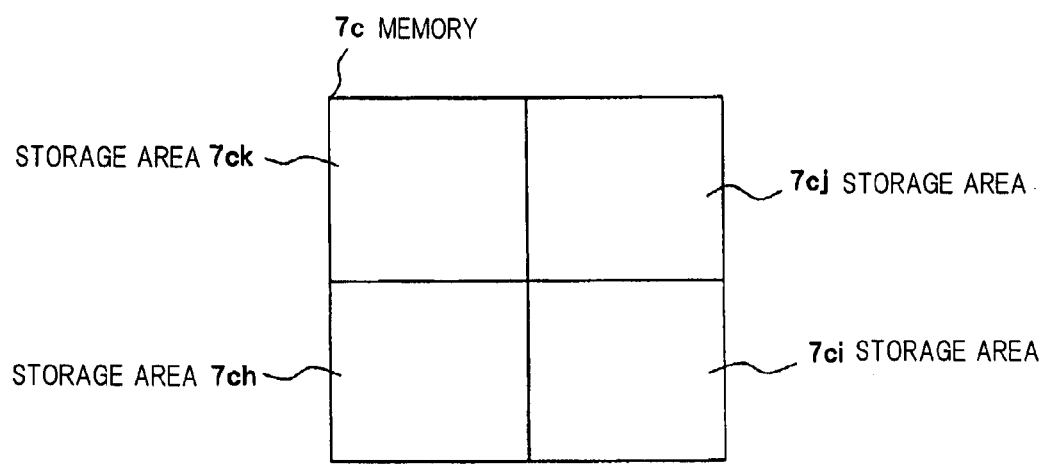
FIG. 20 is a view showing a memory of the gas identifying device shown in FIG. 18.

FIG. 20 shows memory 7c by way of example. As shown in FIG. 20, memory 7c has a plurality of storage areas 7ch, 7ci, 7cj and 7ck.

As shown in FIG. 18, processor 7d processes an output signal from CCD4A with respect to each of color measuring areas 4h through 4k.

Specifically, processor 7d stores the output signal from color measuring area 4h into storage area 7ch, the output signal from color measuring area 4i into storage area 7ci, the output signal from color measuring area 4j into storage area 7cj, and the output signal from color measuring area 4k into storage area 7ck.

Processor 7d integrates output values of components R, G, B of color measuring area 4h respectively. It is assumed that an integrated value of output values of component R is represented by R1, an integrated value of output values of component G by G1, and an integrated value of output values of component B by B1.

Processor 7d then calculates $x=R1/(R1+G1+B1)$ and $y=G1/(R1+G1+B1)$. Processor 7d applies calculated x and y to x and y coordinates of the chromaticity diagram stored in color information storage unit 7a to identify the color of reaction surface 10h.

Then, processor 7d identifies coordinates closest to the identified x and y coordinates of the chromaticity diagram, from the coordinates stored in gas information storage unit 7b. Processor 7d reads the gas identifying information associated with the identified coordinates from gas information storage unit 7b.

Then, processor 7d controls display unit 8 to display the color of reaction surface 10h and the gas identifying information.

Processor 7d also processes output signals from other color measuring areas 4i, 4j and 4k in the same manner as with color measuring area 4h.

Operation of gas identifying device 1000b according to the second embodiment will be described below.

Gas identifying device 1000b operates essentially according to the flowchart shown in FIG. 7.

Therefore, steps 703 and 704 based on a feature of the second embodiment will mainly be described below.

In step 703, processor 7d integrates respective output values of components R, G and B of color measuring area 4h, thereby calculating integrated values R1, G1 and B1.

Processor 7d then calculates $x=R1/(R1+G1+B1)$ and $y=G1/(R1+G1+B1)$. Processor 7d applies calculated x and y to x and y coordinates of the chromaticity diagram stored in color information storage unit 7a to identify the color of reaction surface 10h. Processor 7d also processes output signals from other color measuring areas 4i, 4j and 4k in the same manner as with color measuring area 4h.

After having identified the colors of reaction surfaces 10h through 10k, processor 7d executes step 704.

In step 704, processor 7d identifies the coordinates closest to the coordinates obtained as representing the color of reaction surface 10h from the coordinates stored in gas information storage unit 7b. Processor 7d reads the gas identifying information associated with the identified coordinates from gas information storage unit 7b. Processor 7d also processes output signals from other color measuring areas 4i, 4j and 4k in the same manner as with color measuring area 4h.

According to the second embodiment, processor 7d identifies the colors of the reaction surfaces based on components R, G and B of the colors of the reaction surfaces. Therefore, the colors of the reaction surfaces can be identified with high accuracy.

According to the second embodiment, furthermore, processor 7d identifies a gas to be identified which has chemically reacted with the chemical reagents on the reaction surfaces, based on components R, G, B of the colors of the reaction surfaces. Therefore, the gas to be identified can be identified with high accuracy.

While a preferred embodiment of the present invention has been described using specific terms, such description is for illustrative purposes only, and it is to be understood that changes and variations may be made without departing from the spirit or scope of the following claims.

What is claimed is:

1. A color identifying device comprising:
a mount block for mounting a board to be measured which comprises a plurality of surfaces to be simultaneously measured in predetermined positions, respectively;
a color detector comprising a plurality of color measuring areas corresponding respectively to said surfaces while said board is mounted on said mount block;
a lens for simultaneously forming respective images of said surfaces of said board mounted on said mount block, respectively on said color measuring areas corresponding respectively to said surfaces;
a linear variable filter (LVF) arranged such that output signals from said color measuring areas vary depending respectively on colors of said surfaces; and
a color identifier for identifying colors of said surfaces which correspond respectively to said color measuring areas, based on output signals from said color measuring areas corresponding respectively to said surfaces.

2. The color identifying device according to claim 1, wherein said output signals from said color measuring areas represent spectrums of the colors of said surfaces which correspond respectively to said color measuring areas.

3. The color identifying device according to claim 1, wherein said output signals from said color measuring areas represent three components of the colors of said surfaces which correspond respectively to said color measuring areas.

4. The color identifying device according to claim 3, wherein said output signals from said color measuring areas represent red, green and blue components of the colors of said surfaces which correspond respectively to said color measuring areas.

5. A gas identifying device comprising:
a mount block for mounting a reactive board having a plurality of reaction surfaces disposed in predetermined positions, respectively, said reaction surfaces comprising colors variable by chemical reactions between a gas to be identified and chemical reagents;
a color detector comprising a plurality of color measuring areas corresponding respectively to said reaction surfaces while said board is mounted on said mount block;
a lens for forming respective images of said reaction surfaces of said board mounted on said mount block, respectively on said color measuring areas corresponding respectively to said surfaces; and
a gas identifier for identifying said gas based on output signals from said color measuring areas corresponding respectively to said surfaces.

6. The gas identifying device according to claim 5, wherein said output signals from said color measuring areas represent spectrums of the colors of said reaction surfaces which correspond respectively to said color measuring areas.

7. The gas identifying device according to claim 5, wherein said output signals from said color measuring areas represent three components of the colors of said reaction surfaces which correspond respectively to said color measuring areas.

8. The gas identifying device according to claim 7, wherein said output signals from said color measuring areas represent red, green and blue components of the colors of said reaction surfaces which correspond respectively to said color measuring areas.

9. The color identifying device according to claim 1, further comprising a light emitting element which simultaneously applies a light to said surfaces.

10. The color identifying device according to claim 9, wherein said mount block prevents other lights from irradiating said surfaces, and said other lights are different from the light emitted from said light emitting element.

11. The color identifying device according to claim 1, wherein said LVF filters light such that light passed through to each of said color measuring areas comprises a spectrum of the color of the surface corresponding to said each color measuring area.

12. The color identifying device according to claim 1, wherein said LVF comprises a multilayer film disposed on a glass substrate.

13. The color identifying device according to claim 12, wherein said multilayer film is progressively thicker from one end to another end.

14. The color identifying device according to claim 13, wherein said LVF passes light in a wavelength range from 380 nm to 720 nm.

15. The color identifying device according to claim 1, further comprising a processor generating color information representing a most similar color to each color identified by said color identifier.

16. A color identifying device comprising:
a plurality of surfaces to be simultaneously measured;
a color detector having a plurality of color measuring areas corresponding respectively to said surfaces;
a lens for simultaneously forming images of said surfaces on said color measuring areas corresponding respectively to said surfaces; and
a color identifier identifying colors of said surfaces which correspond respectively to said color measuring areas.

17. The color identifying device according to claim 16, wherein said lens comprises a cylindrical lens.

18. The color identifying device according to claim 16, further comprising a processor generating color information representing a most similar color to each color identified by said color identifier.

19. The color identifying device according to claim 16, further comprising a linear variable filter (LVF) arranged such that output signals from said color measuring areas vary depending respectively on colors of said surfaces.

20. The color identifying device according to claim 19, wherein spectrums of said surfaces comprise mutually different spectrums of colors to be identified.

21. The color identifying device according to claim 11, wherein said spectrums comprise mutually different spectrums of colors to be identified.

* * * * *